United States Patent
Aoki et al.

(10) Patent No.: US 12,194,154 B2
(45) Date of Patent: Jan. 14, 2025

(54) METHOD FOR PRODUCING HYDROGEL MICROCAPSULES, KIT FOR PRODUCING CAPSULES, AND USE THEREFOR

(71) Applicant: RIKEN, Saitama (JP)

(72) Inventors: Hiroyoshi Aoki, Saitama (JP); Yutaka Yamagata, Saitama (JP); Moriya Ohkuma, Saitama (JP); Masahiro Yuki, Saitama (JP)

(73) Assignee: RIKEN, Saitama (JP)

( * ) Notice: Subject to any disclaimer, the term of this patent is extended or adjusted under 35 U.S.C. 154(b) by 794 days.

(21) Appl. No.: 17/437,249

(22) PCT Filed: Mar. 12, 2020

(86) PCT No.: PCT/JP2020/010927
§ 371 (c)(1),
(2) Date: Sep. 8, 2021

(87) PCT Pub. No.: WO2020/184680
PCT Pub. Date: Sep. 17, 2020

(65) Prior Publication Data
US 2022/0168227 A1 Jun. 2, 2022

(30) Foreign Application Priority Data
Mar. 12, 2019 (JP) ................. 2019-044925

(51) Int. Cl.
*A61K 9/50* (2006.01)
*A61K 31/711* (2006.01)
*A61K 35/66* (2015.01)

(52) U.S. Cl.
CPC .......... *A61K 9/5036* (2013.01); *A61K 9/5089* (2013.01); *A61K 31/711* (2013.01); *A61K 35/66* (2013.01)

(58) Field of Classification Search
None
See application file for complete search history.

(56) References Cited

U.S. PATENT DOCUMENTS

| 2008/0031962 A1 | 2/2008 | Boyan et al. |
| 2009/0202640 A1 | 8/2009 | Paoletti et al. |

FOREIGN PATENT DOCUMENTS

| CN | 104887643 | 9/2015 |
| JP | 2008-515434 | 5/2008 |
| JP | 2009-537268 | 10/2009 |

OTHER PUBLICATIONS

Hiroyoshi Aoki et al., "Agarose gel microcapsules enable easy-to-prepare, picolitre-scale, single-cell genomics, yielding high-coverage genome sequences", Scientific Reports, (2022) 12:17014, 13 pages https://doi.org/10.1038/s41598-022-20923-z.

(Continued)

*Primary Examiner* — Jeffrey D Washville
(74) *Attorney, Agent, or Firm* — Casimir Jones, S.C.; Robert A. Goetz

(57) ABSTRACT

A method for producing a capsule, including cooling a suspension so as to gel a thermoresponsive polymer including a core 8 formed from a gel of an ionically-bonded polymer and form a shell (17) of a hydrogel, the suspension being obtained by suspending, in oil (10), a sol (9) of the thermoresponsive polymer, and then using a chelating agent to solate the core so as to hollow out the inside.

15 Claims, 8 Drawing Sheets

(56) References Cited

OTHER PUBLICATIONS

Hiroyoshi Aoki and Yutaka Yamagata, "Agarose Gel Microcapsule : Pico-liter scale DNA Amplification Microvessel for Single Cell Genomics". Multi-omics for Microbiomes-EMSL Integration Conference, Aug. 1-3, 2017, Pasco, WA, 1 page.
Reis, C. P. et al., Review and current status of emulsion/dispersion technology using an internal gelation process for the design of alginate particles, Journal of Microencapsulation, (2006), 23(3), pp. 245-257.
International Search Report of PCT/JP2020/010927, mailed May 26, 2020, 2 pages.
International Preliminary Report on Patentability of PCT/JP2020/010927, mailed Aug. 25, 2021, 7 pages.
Hiroyoshi Aoki et al., "Agarose Gel Microcapsules Enable Easy-to-prepare, Picolitre-scale Single-cell Genomics, Yielding Near-complete Genome Sequences", Research Square, Feb. 3, 2022, 51 pages DOI: https://doi.org/10.21203/rs.3.rs-147972/v2.

| | | |
|---|---|---|
| WGA+ | 4.6 ± 2.9 | ×10⁵ AGMS/BATCH |
| | 8.9 ± 0.9 | % |
| WGA+ / E. coli + | 93.8 ± 8.8 | % |

METHOD FOR PRODUCING HYDROGEL MICROCAPSULES, KIT FOR PRODUCING CAPSULES, AND USE THEREFOR

TECHNICAL FIELD

The present invention relates to a method for producing a hollow hydrogel microcapsule, a kit for producing a capsule, and a use of the hollow hydrogel microcapsule.

BACKGROUND ART

Microcapsules are widely used for, for example, recording materials, medicines, cosmetics, pesticides, and cell transplantation studies due to their capability of controlling, for example, morphology, reactivity, and an influence on external pressure of substances encapsulated in the microcapsules. Many of these microcapsules have an outer shell (shell) that coats the content with an insoluble polymer, and stably retain the content in the shell (at a core) (Ao Z, Langmuir, et. al., 2009, 25, 2572). In contrast, a hollow hydrogel microcapsule that has a shell of a low molecular weight permeable hydrogel instead of an insoluble polymer and has a core in aqueous solution form has various advantages that are not possessed by conventional microcapsules. For example, enzymatic genome amplification of a microorganism or a cell embedded in a core of a hollow hydrogel microcapsule causes a reaction in a minute space. This is expected to remedy nonuniformity during amplification (an amplification bias), which is a conventional problem (Lasken RS, 2012, Nat.Rev.Microbiol., 10, 631).

Cell transplantation with use of a cell embedded in a hollow hydrogel microcapsule achieves transmission of oxygen and nutrients while preventing attack from an immune system cell, and an environment closer to in vivo conditions can be reproduced by mutual cell adhesion and construction of an intercellular network. This makes it possible to expect a higher retention rate of transplanted cells. Thus, various hollow hydrogel microcapsules have been studied (Rabanel JM, 2009, Biotechnol.Prog., 25, 946).

Among the various hollow hydrogel microcapsules, a hollow hydrogel microcapsule having an agarose shell (an agarose gel microcapsule (AGM)) has superior characteristics, such as a superior mechanical strength, superior stability, lower antigenicity, and higher safety, as compared with other hydrogel microcapsules. A hollow hydrogel microcapsule that has been mainly reported has alginate gel microbeads as a core and has a shell formed on a surface of the core by ionic bonding with a cationic polymer such as poly-L-lysine or chitosan (Published Japanese Translation of PCT International Application Tokuhyo No. 2012-525338, Published Japanese Translation of PCT International Application Tokuhyo No. 2009-537268, and Published Japanese Translation of PCT International Application Tokuhyo No. 2008-515434). Such a hollow hydrogel microcapsule is relatively easily prepared but has a poor physical strength due to its shell having a thickness as thin as not more than 1 μm, and the shell is unfortunately easily dissolved by a reagent that is used to carry out DNA amplification, such as strong alkali or high-concentration salt. Thus, an AGM is required which has a thickness of several 10 μm and a physical strength that prevents the AGM from being easily broken when sucked by a micropipette and which is stable even with acid, alkali, and high-concentration salt.

However, it has been difficult so far to easily prepare AGMs. AGMs can be prepared by, for example, the following method. First, alginate gel microbeads are prepared by an emulsification internal gelation method (Emulsification-Internal Gelation, Reis CP, J. Microencapsulation, 2006, 23, 245). Next, heat-dissolved agarose and alginate beads are mixed, and agarose is cooled and gelled in an emulsion with oil. Finally, alginate is solubilized by EDTA so that AGMs are prepared. However, actually, in a case where agarose is allowed to stand and gelled, agarose and alginate beads are precipitated, so that an amorphous gel is formed. In contrast, in a case where agarose and alginate beads are gelled, while being stirred with oil, so as not to be precipitated, spherical AGMs are obtained. However, many of those AGMs adhere to each other during the stirring and form an amorphous aggregated gel. Furthermore, under vigorous stirring conditions, agarose and alginate beads are unfortunately separated from each other.

Therefore, a method of adding a gelling agent to oil has been developed so that precipitation and/or aggregation of minute droplets of a suspension of agarose and alginate beads will be prevented (Non-patent Literature 1). In an emulsion of the suspension of agarose and alginate beads and oil, the oil was solidified first by the gelling agent, and then droplets of the agarose were gelled by cooling. This prevented precipitation and/or aggregation of agarose minute droplets, so that spherical AGMs were obtained. However, an oil gel had a high melting point and thus needed to be heated to 60° C. to 70° C. while being mixed with the suspension of agarose and alginate beads. Thus, a microorganism or a cell that is embedded in an AGM might die out due to heat of the oil gel. Furthermore, in a gene analysis, thermal damage to a microorganism or a cell might lead to leakage of DNA to outside the cell and/or damage to DNA (Non-patent Literature 2). Thus, a method of preparing an AGM at a normal temperature has been required so that damage to a microorganism or a cell to be embedded in the AGM will be prevented.

CITATION LIST

Patent Literatures

[Patent Literature 1]
Published Japanese Translation of PCT International Application Tokuhyo No. 2012-525338, MICROPHARMA LIMITED et al., "BACTERIAL COMPOSITIONS FOR PROPHYLAXIS AND TREATMENT OF DEGENERATIVE DISEASE"

[Patent Literature 2]
Published Japanese Translation of PCT International Application Tokuhyo No. 2009-537268, UNIVERSITA DEGLI STUDI DI TRIESTE, "HYDROGELS OF POLYSACCHARIDE MIXTURES FOR TISSUE ENGINEERING AND AS CARRIERS OF ACTIVE COMPOUNDS"

[Patent Literature 3]
Published Japanese Translation of PCT International Application Tokuhyo No. 2008-515434, GEORGIA TECH RESEARCH CORPORATION "MICROENCAPSULATION OF CELLS IN HYDROGELS USING ELECTROSTATIC POTENTIALS"

Non-Patent Literatures

[Non-patent Literature 1]
Hiroyoshi Aoki and Yutaka Yamagata, "Agarose Gel Microcapsule: Pico-liter scale DNA Amplification Microvessel for Single Cell Genomics". Multi-omics for Microbiomes-EMSL Integration Conference, Aug. 1-3, 2017, PASCO, WA

[Non-patent Literature 2]
Jun SAWAI et al., Japanese Journal of Food Microbiology, 12, 79 (1995)

SUMMARY OF INVENTION

Technical Problem

AGMs can be prepared as below. Specifically, minute droplets of a mixed solution of (i) alginate beads forming a core and (ii) heat-dissolved agarose are gelled in oil, and then alginate is solated by EDTA. Thus, the AGMs can be prepared. However, in oil, minute droplets of alginate and agarose are precipitated and/or aggregated while being allowed to stand, or cause separation of alginate beads and agarose during stirring. Thus, no easy and efficient preparation method has been available.

In this regard, the method disclosed in Non-patent Literature 1 prevents precipitation and/or aggregation of minute droplets of alginate beads and agarose by gelation of oil. Further, gelling the minute droplets by allowing the minute droplets to stand also prevents separation of alginate beads and agarose.

However, in order to prevent gelation of oil, it is necessary to heat an oil gel to 60° C. to 70° C. when the oil gel is suspended with a mixed solution of alginate beads and agarose. Thus, from the viewpoint of avoidance of thermal damage, a microorganism or a cell is required to be embedded in an AGM by an agarose gelation method that prevents mutual precipitation and/or aggregation of minute droplets of alginate beads and agarose at a normal temperature.

Solution to Problem

The present invention has been made in view of the problems, and an object of the present invention is to provide a capsule producing technique and its related technique.

1) A method for producing a hydrogel capsule including (i) a core containing an ionically-bonded polymer and (ii) a shell containing a thermoresponsive polymer, the method including:

(a) dispersing, in a first oil phase, a sol (aqueous phase) of the thermoresponsive polymer including a core at least a surface of which is formed from a gel of the ionically-bonded polymer, and cooling the sol so as to gel the thermoresponsive polymer and form the shell, oil, contained in the first oil phase, having a hydrophobicity, as measured by an octanol-water partition coefficient (Log $P_{ow}$), of not less than 3 and having a specific gravity and a viscosity that satisfy the following formula:

$$\rho_p - \rho_f \leq \frac{18(100-x)L}{100tD_p^2 g}\eta$$

wherein $\rho_p$ represents an average specific gravity [kg/m³] of an ionically-bonded polymer gel and a thermoresponsive polymer sol; $\rho_f$ represents an oil specific gravity [kg/m³]; x represents a yield [%] obtained in a step of producing the hydrogel capsule; L represents a depth [m] of the suspension that is contained in a vessel; t represents a gelling time [s] of the thermoresponsive polymer; $D_p$ represents a diameter [m] of the hydrogel capsule; g represents gravitational acceleration [m/s²]; and η represents an oil viscosity [Pa·s].

Advantageous Effects of Invention

AGMs are excellent in mechanical strength, stability, and safety, and are expected to be used for various applications such as a genetic engineering application and a medical application (e.g., cell transplantation). An aspect of the present invention makes it possible to provide a technique for producing a hollow hydrogel microcapsule, the technique being capable of stably storing the hollow hydrogel microcapsule while preventing or reducing damage to and/or contamination of a target object.

DESCRIPTION OF EMBODIMENTS

<1. Method for Producing Microcapsule>

Figure 1:
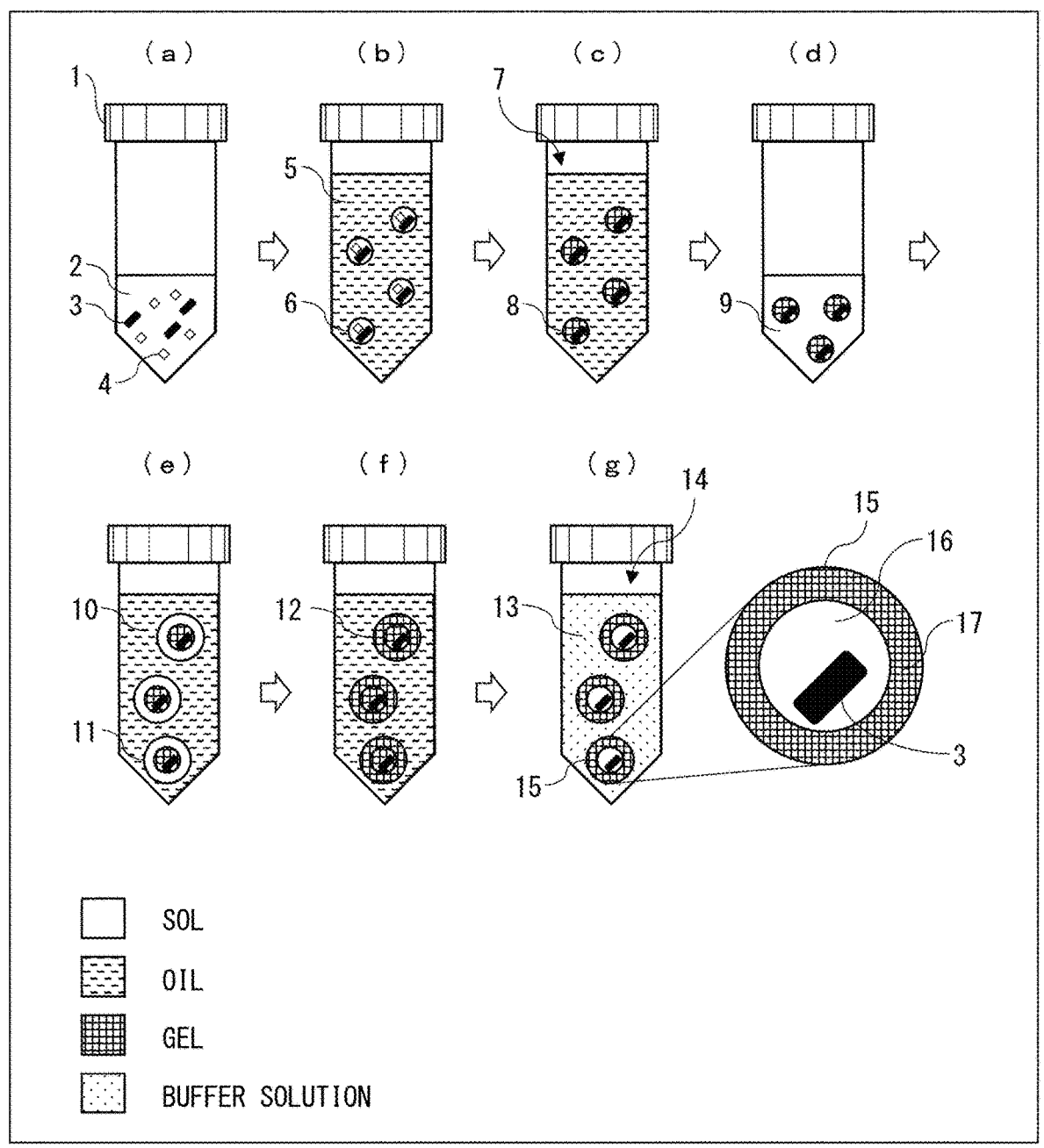
FIG. 1 is a view for schematically describing a process for preparing a hollow hydrogel microcapsule in accordance with an aspect of the present invention. (a) of FIG. 1 illustrates a step of preparing a suspension of an ionically-bonded polymer sol containing an embedding target object. (b) of FIG. 1 illustrates a step of preparing minute droplets of the ionically-bonded polymer sol by emulsification into oil. (c) of FIG. 1 illustrates a step of gelling the ionically-bonded polymer sol. (d) of FIG. 1 illustrates a suspension of ionically-bonded polymer gel beads and a thermoresponsive polymer sol. (e) of FIG. 1 illustrates a step of preparing minute droplets of the thermoresponsive polymer sol. (f) of FIG. 1 illustrates a step of forming a shell onto a core of an ionically-bonded polymer gel by gelation of a thermoresponsive polymer. (g) of FIG. 1 illustrates a step of hollowing out thermoresponsive polymer gel beads by solation of the core of the ionically-bonded polymer gel.

The following description will more specifically discuss, with reference to FIG. 1, a method for producing a hollow hydrogel microcapsule (capsule) 15 in accordance with an aspect of the present invention.

As illustrated in (a) to (g) of FIG. 1, the method for producing the capsule 15 in accordance with an aspect, the capsule 15 including a core 16 of an ionically-bonded polymer sol and a shell 17 of a gel of a thermoresponsive polymer, includes a step of gelling a sol 6 of an ionically-bonded polymer ((c) of FIG. 1), a step of gelling a thermoresponsive polymer so as to form the shell 17 ((f) of FIG. 1), and a step of solating an ionically-bonded polymer gel 8 inside the capsule ((g) of FIG. 1).

[1-1: Step of Gelling Sol of Ionically-Bonded Polymer]

In a step of gelling a sol of an ionically-bonded polymer, embedding target objects 3 (*E. coli* in the present example) and ion sources 4 (calcium carbonate powder in the present example) are suspended with respect to an ionically-bonded polymer sol 2 in a vessel 1 that is closed ((a) of FIG. 1). Next, those suspended matters in the ionically-bonded polymer sol 2 are emulsified and dispersed in oil (a second oil phase) 5 so that minute droplets 6 of the ionically-bonded polymer sol are formed ((b) of FIG. 1). The minute droplets 6 contain the embedding target objects 3 (described earlier) and the ion sources 4 (described earlier). Subsequently, organic acid 7 (acetic acid in the present example) is added to the oil 5 so that the ion sources 4 (calcium carbonate) are dissolved by the organic acid and alkaline earth metal ions (calcium ions in the present example) are liberated. The liberated alkaline earth metal ions gel the minute droplets 6 formed from the ionically-bonded polymer sol 2 so that beads 8 are formed ((c) of FIG. 1). The beads 8 are collected from the oil 5 and washed, and then are subjected to the subsequent step.

(Ionically-Bonded Polymer)

The ionically-bonded polymer is a water-soluble polymer and is capable of crosslinking a part of a main chain of a polymer via ionic bonding. The sol 2 prepared by dissolving the ionically-bonded polymer in an aqueous solvent is crosslinked and gelled by ionic bonding when supplied with ions. Such an ionically-bonded polymer is a polymer that reversibly causes a sol-gel transition by ions supplied into a system containing the ionically-bonded polymer, regardless of the temperature of the system. The ionically-bonded polymer is therefore preferable because even the ionically-bonded polymer that is mixed in a solating thermoresponsive polymer by warming can suitably maintain its gel state.

The ionically-bonded polymer is, for example, at least one kind of ionically-bonded polymer that forms a reversible gel and that is selected from the group consisting of a polysaccharide having a cationic or anionic functional group in a molecule, such as alginate, deacylated gellan gum, polyacrylic acid, and carboxymethylcellulose, and is crosslinked by counter ions and gelled. Note that the aqueous solvent for dissolving the ionically-bonded polymer so as to prepare the sol can be a buffer solution.

(Ion Source)

An ion source 4 for releasing counter ions for gelling a sol of the ionically-bonded polymer can be exemplified by salts of alkaline earth metals such as calcium, magnesium, strontium, barium, and zinc, and is preferably a calcium salt, for example. Examples of the calcium salt include calcium carbonate, calcium citrate, and calcium phosphate. In particular, calcium carbonate that is insoluble under neutral conditions and is uniformly soluble under weak acidic conditions at a pH of approximately 5 is preferable. Thus, calcium carbonate that is dispersed into an ionically-bonded polymer sol adjusted to neutral conditions (approximately pH 6.5 to 7.5) and is emulsified in oil is uniformly dispersed without forming a gel. Addition of organic acid after the emulsification causes calcium ions to be generated by dissolution of calcium carbonate in droplets in the oil, so that the ionically-bonded polymer is gelled, and uniform beads of a hydrogel are formed.

According to a method for producing a capsule in accordance with an aspect, a target object to be embedded in a sol of an ionically-bonded polymer is suspended at a stage of preparing the sol of the ionically-bonded polymer.

(Oil for Dispersing Ionically-Bonded Polymer)

Minute droplets of the ionically-bonded polymer are formed by dispersing the ionically-bonded polymer sol 2 into the oil 5. Note here that the oil 5 that is an oil phase (is also a continuous phase) preferably contains a surfactant.

The oil 5 only needs to allow the sol of the ionically-bonded polymer to be dispersed in droplet form. Examples of the oil 5 include saturated or unsaturated higher fatty acids, alkyl ester, polyglycerol ester, glyceride of these higher fatty acids, and saturated or unsaturated higher aliphatic alcohols, and aliphatic hydrocarbons. More specifically, the oil can be, for example, any of vegetable oils such as salad oil, cottonseed oil, soybean oil, and corn oil (glycerides of saturated or unsaturated higher fatty acids). Examples of the oil include fatty acids such as caprylic acid, lauric acid, palmitic acid, oleic acid, and stearic acid, and, as alkyl esters of these fatty acids, methyl caprylate, methyl laurate, methyl palmitate, methyl oleate, methyl stearate, and ethyl stearate. Furthermore, examples of an ester of such a fatty acid and polyglycerol include an ester of, for example, octacaprylic acid-6-polyglyceride (PGO). Examples of higher aliphatic alcohols include caprylic alcohol, lauryl alcohol, oleyl alcohol, stearyl alcohol, and isostearyl alcohol. Examples of an aliphatic hydrocarbon include icosane. Alternatively, the oil can be, for example, silicone oil or modified silicone oil into which a functional group such as a phenyl group, an amino group, or a carboxyl group has been introduced. Among these, the oil is preferably a saturated or unsaturated higher aliphatic alcohol, and more preferably isostearyl alcohol because such an alcohol is a chemical synthetic oil in which a microorganism is less likely to be mixed, is highly safe, is easily removed by centrifugation or washing, and acetic acid for use in gelation is easily dissolved therein.

(Surfactant)

It is preferable to use a w/o emulsion-forming surfactant as the surfactant in order to emulsify and disperse, into the oil, the droplets of the sol of the ionically-bonded polymer contained in the aqueous solvent. The surfactant can be any of a cationic surfactant, an anionic surfactant, an amphoteric surfactant, and a nonionic surfactant provided that the surfactant can form the w/o emulsion. Examples of the surfactant include a naturally-derived surfactant and a synthetic surfactant. Examples of the naturally-derived surfactant include lecithin. Examples of the synthetic surfactant include sorbitan monolaurate (Span (Registered Trademark) 20), sorbitan monopalmitate (Span (Registered Trademark) 40), sorbitan monostearate (Span (Registered Trademark) 60), sorbitan tristearate (Span (Registered Trademark) 65), sorbitan monooleate (Span (Registered Trademark) 80), sorbitan sesquioleate (Span (Registered Trademark) 83), sorbitan trioleate (Span (Registered Trademark) 85), and sorbitan isostearate (Span (Registered Trademark) 120). Examples of the synthetic surfactant also include polyoxyethylene sorbitan monolaurate (Tween (Registered Trademark) 20), polyoxyethylene sorbitan monolaurate (Tween (Registered Trademark) 21), polyoxyethylene sorbitan monopalmitate (Tween (Registered Trademark) 40), polyoxyethylene sorbitan monostearate (Tween (Registered Trademark) 60), polyoxyethylene sorbitan monostearate (Tween (Registered Trademark) 61), polyoxyethylene sorbitan tristearate (Tween (Registered Trademark) 65), and polyoxyethylene sorbitan monooleate (Tween (Registered Trademark) 80).

By thus adding the surfactant to the oil 5, it is possible to improve dispersibility of the ionically-bonded polymer sol and to prevent or reduce fusion of the sol droplets 6. From this viewpoint, the surfactant contained in the oil can have a concentration in a range of 0.5% to 5%.

Stirring during dispersion of the sol of the ionically-bonded polymer into the oil 5 can be designed as appropriate by a scale on which the sol droplets 6 of the ionically-bonded polymer are prepared, and is not limited. Note, however, that, in order to disperse the sol of the ionically-bonded polymer into the oil in a 50 mL conical tube, it is possible to carry out the stirring by, for example, hand or a voltex mixer.

(Organic Acid)

After the stirring, the organic acid 7 is supplied in a state in which the droplets 6 of the ionically-bonded polymer sol are emulsified and dispersed into the oil 5. The organic acid 7 thus supplied allows liberation of alkaline earth metal ions such as calcium ions or magnesium ions from an alkaline earth metal salt, which is the ion source 4 contained in a minute droplet 6 of the ionically-bonded polymer, so that the ionically-bonded polymer is gelled, and the beads 8 of a hydrogel are obtained (see (c) of FIG. 1). The organic acid 7 that is used to gel the ionically-bonded polymer sol can be acid that is dissolved in the oil 5 and is soluble in an organic solvent. Examples of such acid include acetic acid, citric acid, and lactic acid (in (c) of FIG. 1, acetic acid is used). In a case where the beads 8 of the gel of the ionically-bonded polymer are formed, while the shell 17 of the thermoresponsive polymer is being formed later, an agarose sol of the shell is prevented from permeating into a central part of a microcapsule, and the core 16 that is hollow is formed.

The beads 8 of the ionically-bonded polymer that has been gelled can be suitably collected from the oil 5 by filtration or by removal by washing with a buffer solution containing a surfactant ((d) of FIG. 1). The filtration can be carried out with use of, for example, a mesh filter having a diameter of 10 μm to 100 μm. Furthermore, the surfactant such as polyoxyethylene sorbitan monolaurate (described earlier) is preferably added to the buffer solution because the surfactant can remove the oil 5. Moreover, an organic solvent such as ether or alcohol can be used for washing in a case where the microcapsule is not used for culture of the embedding target object, but is used for, for example, gene amplification. Note here that examples of the ether include diethyl ether and dibutyl ether and that examples of the alcohol include lower alkyl alcohols having approximately 1 to 8 carbon atoms.

[1-2: Another Step of Gelling Sol of Ionically-Bonded Polymer]

According to the method for producing a capsule in accordance with an aspect, the emulsification internal gelation method (described earlier) carried out with use of the ionically-bonded polymer sol and the oil is used in the step of gelling the sol of the ionically-bonded polymer. Note, however, that hydrogel beads of the gel of the ionically-bonded polymer can be formed by a method that is not limited to the above method.

The step of gelling the sol of the ionically-bonded polymer into beads form can be carried out by not only the emulsification internal gelation method but also a discharge method of dropping droplets of alginate, through a nozzle, into a coagulating agent such as calcium chloride, or a method of coagulation in a microchannel (Rabanel JM, 2009). As compared with the emulsification internal gelation method, the discharge method or a microchannel method further makes it possible to prepare hydrogel beads having a uniform particle size. Note, however, that the discharge method and the microchannel method need to be carried out by dedicated devices, many of which are not commercially available and are difficult to obtain. Furthermore, in embedding a microorganism or a cell in a hydrogel bead, it is necessary to carry out sterilization with respect to these devices in order to prevent other microorganism(s) from being mixed in the hydrogel bead. In contrast, the emulsification internal gelation method is highly convenient because it does not require any particularly complicated device and allows the hydrogel beads to be prepared in a commercially-available inexpensive disposable vessel that has been subjected to sterilization.

[2: Step of Forming Shell 17 of Thermoresponsive Polymer Gel]

In the step of forming the shell 17, first, the beads 8 of the ionically-bonded polymer gel are suspended in a sol 9 of the thermoresponsive polymer ((d) of FIG. 1). Then, a suspension of the thermoresponsive polymer sol 9 and oil are emulsified so that minute droplets 11 of the thermoresponsive polymer sol 9 which minute droplets 11 contain the ionically-bonded polymer gel beads 8 are prepared ((e) of FIG. 1). These minute droplets are ice-cooled so that the thermoresponsive polymer sol is gelled ((f) of FIG. 1). The gelled thermoresponsive polymer sol is collected from the oil 10, washed, and then suspended in a buffer solution 13 ((g) of FIG. 1).

(Thermoresponsive Polymer)

The thermoresponsive polymer is a material that exhibits reversible sol-gel transition, not depending on whether ions are present in a system containing the thermoresponsive polymer, but at a predetermined temperature serving as a sol-gel transition boundary. A material for forming the shell of the thermoresponsive polymer is preferably a material that is transparent under visible light and hydrophilic, and examples of such a material include agarose, agar, carrageenan (kappa type is preferable), and native gellan gum, and more preferable examples of the material include agarose, agar, gelatin, and carrageenan. Agarose, agar, or gelatin is more preferably used, and agarose is most preferably used.

(Gelling Material Different from Thermoresponsive Polymer)

(i) A polymer that is different from the ionically-bonded polymer and the thermoresponsive polymer and that has a gelling ability, or (ii) a polymer to which a crosslinking agent is added can also be used for the shell. Examples of the polymer (i) include acid-solubilized collagen that gelates as it is neutralized. Examples of the polymer (ii) include chemical crosslinking reagents such as glutaraldehyde and extracellular matrix proteins to which an enzyme crosslinking reagent such as transglutaminase is added, such as collagen, gelatin, elastin, fibronectin, and laminin. In particular, the enzyme crosslinking reagent is less toxic and allows the shell to be more suitably formed, as compared with the chemical crosslinking reagent. A specific action of thrombin allows fibrin contained in a mixed solution of the thrombin and the fibrin to be gelled. These protein-based matrices can serve as a scaffold for cell adhesion and promote cell adhesion to an inner wall of the shell.

Examples of a characteristic of agarose include 1) a characteristic of allowing a stable gel to be formed even with respect to alkali or salt, 2) a characteristic of being capable of temperature-dependent gelation even at a low temperature (e.g., approximately not more than 40° C.), 3) a characteristic of having a high gel strength and being easy to handle or isolate, without being easily broken by, for example, pipetting, even in hollow and minute microcapsule form, 4) a characteristic of transmitting a low molecular weight molecule such as oligo-DNA, oxygen, an ion, amino acid, peptide, or protein, but not transmitting a macromolecule such as chromosome DNA or a microscale substance such as a cell or a microorganism, 5) a characteristic of being less biologically toxic, 6) a characteristic of being transparent under visible light and allowing a non-fluorescent gel to be formed, 7) a characteristic of allowing a hydrophilic gel to be formed, and 8) a characteristic of being capable of controlling a gelation temperature from approximately 40° C., which is obtained before chemical modification such as 2-hydroxyethyl esterification, to 26° C. to 30° C. by the chemical modification. In particular, from the viewpoint of storage stability and thermal stability of a microcapsule at a room temperature, the thermoresponsive polymer is more preferably a thermoresponsive polymer capable of controlling the gelation temperature from 4° C. to 40° C.

Note that not only agarose but also a thermoresponsive polymer that is used in the present invention preferably has at least one of the characteristics selected from the above 1) to 8).

(Oil for Dispersing Shell of Thermoresponsive Polymer)

A surfactant is preferably contained so that the thermoresponsive polymer sol 9 containing the beads 8 of the ionically-bonded polymer sol is dispersed into the oil 10, and the minute droplets 11 are prepared and gelled by cooling.

The ionically-bonded polymer is gelled by addition of ions in a few seconds, whereas the thermoresponsive polymer is gelled such that intermolecular helix formation, for example gradually proceeds in accordance with a change in temperature and a gel is finally formed over a period of several tens of minutes to approximately one hour (Janaky Narayanan et al., 2006, J. Phys.: Conf. Ser 28 83). Thus, as compared with gelation of the sol droplets 6 of the ionically-bonded polymer, gelation of the minute droplets 11 of the thermoresponsive polymer makes it easier to form an amorphous aggregated gel due to precipitation and/or aggregation. As the oil 10 for forming beads 12 in which the thermoresponsive polymer is gelled, oil that includes features 1) to 4) below is used so that the precipitation and/or aggregation is/are prevented. Though also shown in Example 1, use of the oil including the features 1) and 3) makes it possible to prevent precipitation and coagulation during gelation and to easily prepare a microcapsule. 1) A feature such that (i) a specific gravity difference between the minute droplets and the oil and (ii) an oil viscosity satisfy Formula (3), which is a relation derived from Stokes' Law formula.

Figure 2:
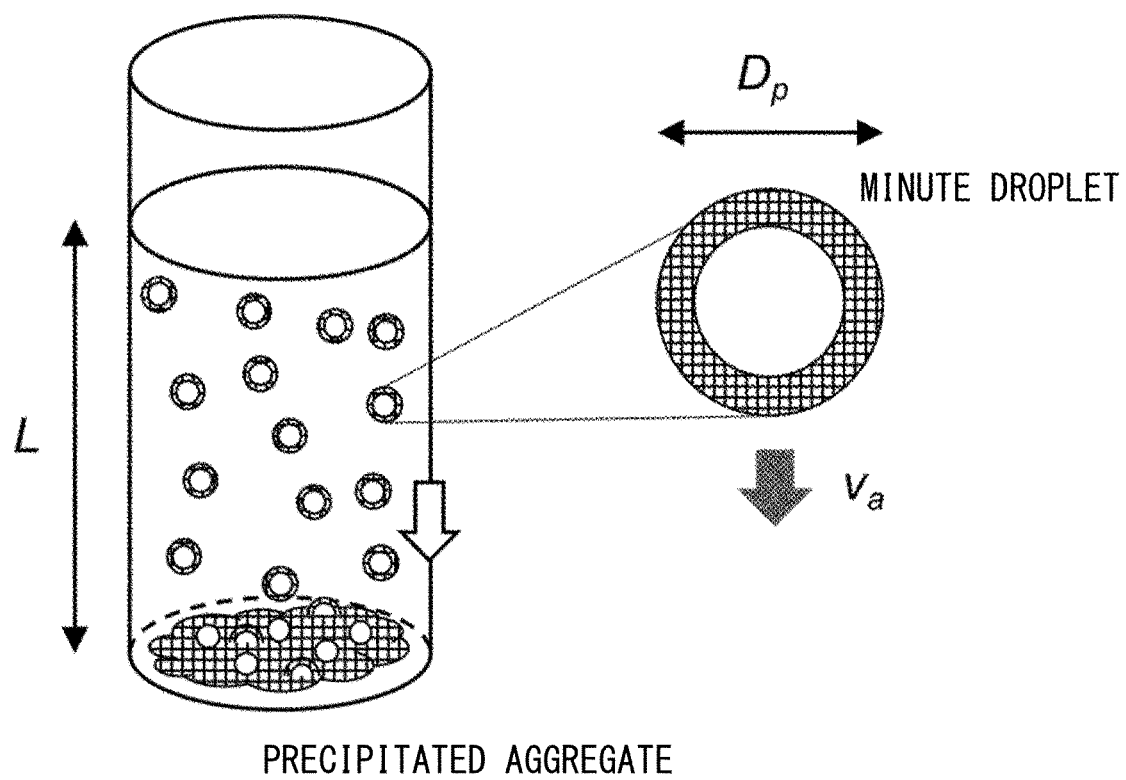
FIG. 2 is a view describing a relationship among (a) a size $D_p$ of a minute droplet, (b) a terminal velocity $v_a$ [m/s] of the minute droplet, (c) a depth L [m] of a suspension of minute droplets and oil, and (d) a gelling time t [s] of a thermoresponsive polymer sol forming a shell in a capsule, the relationship being obtained in a process for preparing a hollow hydrogel microcapsule in accordance with an aspect of the present invention.

Here, a mixed solution of the thermoresponsive polymer sol and gel beads of the ionically-bonded polymer is stirred with the oil in a cylindrical vessel so that the minute droplets are formed. The minute droplets are cooled for a certain period of time and allowed to stand so as to be gelled. The minute droplets that have been allowed to stand start to be gradually precipitated by the specific gravity difference between the minute droplets and the oil, and a resistance due to the viscosity of the oil causes a precipitation velocity of the minute droplets to reach a constant velocity (terminal velocity). The terminal velocity $v_s$ [m/s] of the minute droplets is calculated from Formula (1), which is the Stokes' Law formula (Stokes's Law).

$$v_s = \frac{D_P^2(\rho_p - \rho_f)g}{18\eta} \quad (1)$$

wherein $D_p$ represents a diameter [m] of the minute droplets, $\rho_p$ represents a specific gravity [kg/m³] of the minute droplets, $\rho_f$ represents an oil specific gravity [kg/m³], g represents gravitational acceleration [m/s²], and $\eta$ represents an oil viscosity [Pa·s] (FIG. 2).

Some of the minute droplets are precipitated on the bottom, and an amorphous gel (precipitated aggregate) is formed and cannot be collected (FIG. 2). Assuming that x [%] represents a yield obtained in this step, $v_a$ [m/s] represents a terminal velocity of the minute droplets during the step, L [m] represents a depth of a suspension of the minute droplets and the oil which suspension is contained in a vessel (e.g., a conical tube), and t [s] represents a gelling time of the thermoresponsive polymer sol that forms a shell in a capsule, the following Formula (2) is found.

$$v_a = \frac{L(100-x)}{100t} \quad (2)$$

Then, the following Formula (3) is found from Formulae (1) and (2), and $v_s v_a$.

$$\rho_p - \rho_f \leq \frac{18(100-x)L}{100t D_p^2 g}\eta \quad (3)$$

wherein $\rho_p$ on the left side and a coefficient of $\eta$ on the right side are uniquely determined by a preparation condition. The oil specific gravity $\rho_f$ and the viscosity $\eta$ need to satisfy this formula.

The following description will show a specific example. A 50 mL conical tube was used to gel the minute droplets over approximately 30 minutes and set a yield of the gelled minute droplets to 90%. In so doing, assuming that the depth L of the suspension of the minute droplets and the oil is approximately 40 mm, the diameter $D_p$ of the minute droplets is approximately 100 μm, the specific gravity $\rho_p$ of the minute droplets is 1020 kg/m³ (approximately 2% gel, w/v), and gravitational acceleration is 9.8 m/s², Formula (3) is represented as in the following Formula (4).

$$\rho_f \geq 1020 - 408\eta \quad (4)$$

Assume that the oil viscosity is 0.2 Pa·s, which is a common oil viscosity. In this case, it is found from Formula (4) that the oil specific gravity $\rho_f$ is not less than approximately 857 kg/m³ (0.857 g/mL). In this case, PGO (0.997 g/mL), for example satisfies the present requirement. 2) A feature such that the viscosity at 20° C. is not more than 1000 mPa·s.

According to Formula (3), a higher viscosity n makes it possible to also use oil that has a lighter specific gravity. However, it is actually difficult to uniformly stir highly viscous oil and the thermoresponsive polymer sol. In order to achieve uniform stirring by easily shaking a vessel by, for example, a hand or a voltex mixer, the viscosity of the oil has an upper limit of approximately 1 Pa·s (1000 mPa·s) (a viscosity of, for example, honey).

Specifically, the oil for dispersing the thermoresponsive polymer sol preferably has a viscosity, as measured at 20° C., that satisfies Formula (3) and is not more than 1000 mPa·s. Dispersibility of the minute droplets of the thermoresponsive polymer sol can be suitably maintained under such a condition. Examples of oil that has a viscosity of not more than 1,000 mPa·s in Formula (4) include not only PGO (described earlier) but also liquid synthetic resins such as polybutene (NOF CORPORATION, 015N, 0.870 g/mL, 566 mPa·s); and esters of glycerides, polyglycerides, or polyalcohols, such as polyglycerol-2 triisostearate (Nikko Chemicals Co., Ltd., 0.930 g/mL, 510 mPa·s), castor oil (ITOH OIL CHEMICALS CO., LTD., 0.959 g/mL, 680 mPa·s), pentaerythrityl tetraisostearate (The Nisshin Oillio Group, Ltd., 0.960 g/mL, 420 mPa·s), and polyglycerol-2 tetraisostearate (The Nisshin OilliO Group, Ltd., 0.926 g/mL, 369 mPa·s). Among these oils, PGO, which has the lowest viscosity, is most easily stirred and preferable.

3) A feature such that an octanol-water partition coefficient (Log $P_{ow}$) is not less than 3.

The octanol-water partition coefficient (Log $P_{ow}$) is defined, in a biphasic system of octanol and water, as a ratio between (a) a concentration at which oil is dissolved in an octanol phase and (b) a concentration at which the oil is dissolved in an aqueous phase, and is expressed by a common logarithm. The oil that has a higher Log $P_{ow}$ is more preferable because such oil exhibits hydrophobicity and is separated from the thermoresponsive polymer sol, the thermoresponsive polymer sol is not precipitated by the oil, and a gel is stably formed. The oil that has an octanol-water partition coefficient (Log $P_{ow}$) of not less than 3, and more preferably not less than 6.

4) A feature such that the oil has a melting point of not more than 20° C.

In order to embed a microorganism or a cell, the oil needs to be a liquid, while being mixed with the thermoresponsive polymer sol at a room temperature or 37° C., so as not to cause thermal damage to the microorganism or the cell. The oil thus has a melting point of a room temperature, and more preferably not more than 20° C.

As the oil that includes such features 1) to 4) and is capable of stably dispersing the minute droplets thereinto, a polyol ester, a glycerol ester, a polyglycerol ester, a silicone oil, an aliphatic hydrocarbon, a liquid synthetic resin, castor oil, or the like is preferably selected, and a polyol ester, a glycerol ester, or a polyglycerol ester is more preferably used. Examples of the polyol ester, the glycerol ester, and the polyglycerol ester include esters synthesized from (i) fatty acids having not less than 8 and not more than 20 carbon atoms and (ii) polyalcohol, glycerol, polyglycerol, or the like. Note here that polyglycerol has a polymerization degree in a range of 2 to 15. Examples of silicone that includes the features 1) to 4) and can be used include dimethyl silicone oil (Shin-Etsu Chemical Co., Ltd., KF-96 50 cs to 6000 cs) and methylphenyl silicone oil (Shin-Etsu Chemical Co., Ltd., KF-50). Examples of a liquid synthetic resin include polybutene (NOF CORPORATION, 015N, 3N).

The specifications (features) 1) to 4) can be satisfied by combining a plurality of oils. For example, a less viscous oil having a relatively low specific gravity and a highly viscous oil can be mixed so as to be used. Similarly, oils that differ from each other in specific gravity can be mixed so that an oil specific gravity is adjusted. Note that the oils are preferably prepared so that a difference between the oil specific gravity and a specific gravity of the minute droplets is in a range of ±5%.

It has been explained in 4) (described earlier) that the oil preferably has a melting point of not more than 20° C. However, according to a method for producing a microcapsule in accordance with another aspect, the oil can be another oil that has a temperature of not less than 26° C. to 30° C., which is a temperature at which the thermoresponsive polymer is gelled, and has a temperature of around 37° C., which causes no damage to an organism to be embedded, or a temperature of not more than 37° C., provided that the requirement represented by Formula (3) is satisfied. For example, among the oils listed earlier, such oil can be any of high molecular alkanes such as nonadecane (having a melting point of 32° C.) and eicosane (having a melting point of 36.7° C.), high molecular alcohols such as tridecyl alcohol (having a melting point of 30° C. to 32° C.) and myristyl alcohol (having a melting point of 38° C.), and high molecular esters such as methyl stearate (having a melting point of 37° C.), hexa(hydroxystearate/stearate/rosinate)dipentaerythrithyl (having a melting point of 35° C.), and (ethyl hexanoate/stearate/adipate)glyceryl (having a melting point of 31° C.). Such oil 10 is melted, and the thermoresponsive polymer sol 9 is dispersed and emulsified and then immediately cooled, so that the minute droplets of the thermoresponsive polymer sol can be stably retained in the oil 10 that has been solidified.

In addition, it is possible to mix, with the oil, an oil gelling agent that is exemplified by dextrin fatty acid esters such as dextrin palmitate and dextrin (palmitate/ethyl hexanoate), fatty acids such as 12-hydroxystearate, sorbitol compounds such as 1,3;2,4-dibenzylidene-D-sorbitol, and amino acid derivatives such as N-lauroyl-L-glutamate-α,γ-bis-n-butylamide. With this, the viscosity of the oil can be adjusted so as to be in the above range. The oil gelling agent preferably has a gelation temperature that is higher than the gelation temperature of the thermoresponsive polymer. Specifically, the oil is preferably gelled at a temperature of approximately 30° C. to 40° C. Use of the oil gelling agent allows the minute droplets 11 of the thermoresponsive polymer gel to be stably retained in the oil 10 that has been gelled. In addition to the oil gelling agent, an oil thickener such as 2-aluminium ethyl hexanoate can be similarly used.

(Surfactant)

A w/o emulsion surfactant is used as a surfactant that is added to the oil 10 so that the thermoresponsive polymer sol is emulsified and dispersed. Such a surfactant can be any of the surfactants listed earlier and used to emulsify and disperse the ionically-bonded polymer sol. In particular, it is preferable to use any of the surfactants that have been already described as the synthetic surfactants and are exemplified by sorbitan monolaurate, sorbitan monopalmitate, sorbitan monostearate, sorbitan tristearate, sorbitan monooleate, sorbitan trioleate, sorbitan isostearate, polyoxyethylene sorbitan monolaurate, polyoxyethylene sorbitan monolaurate, polyoxyethylene sorbitan monopalmitate, polyoxyethylene sorbitan monostearate, polyoxyethylene sorbitan monostearate, polyoxyethylene sorbitan tristearate, and polyoxyethylene sorbitan monooleate.

For example, 0.25% to 1% (v/v) sorbitan monooleate can be added in PGO. In a case where sorbitan monooleate having a concentration of not less than 5% is used, it is observed, due to an improvement in emulsification ability, that the droplets of the thermoresponsive polymer sol are made minute and/or that the thermoresponsive polymer sol that has been solidified in the oil and is spherical is broken. In a case where 1-butanol is used for washing, sorbitan monooleate having a concentration of not less than 5% is less easily dissolved in butanol and thus is precipitated. This limits a washing method. Sorbitan monooleate therefore preferably has a concentration of less than 5%.

The surfactants listed earlier can be used in combination as appropriate in accordance with a type of oil.

(Gelation of Thermoresponsive Polymer Sol)

In order to immediately form the shell 17 of the thermoresponsive polymer gel, it is possible to disperse the thermoresponsive polymer sol into the oil 10 at a room temperature and then gel the thermoresponsive polymer sol by mixing the thermoresponsive polymer sol with the oil 10 that has been cooled. In this case, it is possible to not only cool a vessel with, for example, ice but also cool the thermoresponsive polymer sol directly with oil. This allows a reduction in preparation time. It is therefore preferable that the oil phase (i) be cooled in advance to a temperature lower than a temperature at which the thermoresponsive polymer is gelled and (ii) have a temperature in a range of 4° C. to 10° C.

Gelation of the shell of the thermoresponsive polymer results in formation of microcapsules 12 each including a core of the ionically-bonded polymer gel and a shell of the thermoresponsive polymer gel ((f) of FIG. 1). Gelation prevents or reduces fusion or bonding of such microcapsules 12. Thus, as in the case of washing of cores 8 of the ionically-bonded polymer gel, it is possible to suitably collect the microcapsules 12 from the oil 10 by washing with an organic solvent such as ether or alcohol, or by washing with a buffer solution containing a surfactant.

Note here that the organic solvent such as ether or alcohol can be an organic solvent similar to an organic solvent used to wash the cores 8 of the ionically-bonded polymer gel. Note also that, in order to suitably remove the oil phase, it is preferable to mix, with a buffer solution for use in washing, any of the surfactants listed earlier, such as polyoxyethylene sorbitan monolaurate.

[3: Step of Solating Core of Ionically-Bonded Polymer]

According to the method for producing a microcapsule in accordance with an aspect, ions are removed that are contained in the cores 8 of the ionically-bonded polymer gel and are present in the microcapsules 12 suspended in the buffer solution 13 ((g) of FIG. 1). More specifically, in a core 8, alkaline earth metal ions that are exemplified by calcium ions and contribute to crosslinking by ionic bonding are chelated by a chelating agent 14 (in (g) of FIG. 1, ethylenediamine tetraacetic acid (EDTA)) so as to be eluted to outside the shell 17. This results in formation of a hollow hydrogel microcapsule 15 including the core 16 of the ionically-bonded polymer sol and the shell 17 of the thermoresponsive polymer gel ((g) of FIG. 1). In a case where the ionically-bonded polymer is alginate, an enzyme such as alginate lyase can be used to decompose and solate the alginate.

(Other Chelating Agent)

Examples of a chelating agent that is different from EDTA and can be used include various chelating agents such as EGTA, citric acid, oxalic acid, trans-1,2-cyclohexanediamine tetraacetic acid (CyDTA), and nitrilotriacetic acid (NTA).

This makes it possible to obtain the microcapsule 15 that has the core 16 of the ionically-bonded polymer sol in an inner part of the shell 17 of the thermoresponsive polymer gel. Such a microcapsule 15 allows the shell 17 of the thermoresponsive polymer gel to prevent external entry of, for example, a polymer such as chromosome DNA, a virus, bacteria, or a cell into the core 16. This makes it possible to prevent a target object that is embedded in the core 16 in advance from being externally contaminated with, for example, DNA or bacteria. In a case where the target object that is embedded in the core 16 is, for example, DNA, the core 16, which is in sol form, can be further amplified by using DNA as an enzyme throughout the inner part of the shell 17, as compared with the core that is in gel form. In a case where the target object that is embedded in the core 16 is a cell or the like, attack from an immune cell and can be prevented, and mutual adhesion of cells or adhesion of a cell to an inner wall of the shell depending on a material of the shell allows imitation of an environment that is closer to in vivo conditions. This makes it possible to expect a higher survival rate and a higher transplantation efficiency.

In a case where the core 8 of the ionically-bonded polymer gel is caused to contain a skeleton material (e.g., a fiber or the like) that is insoluble in the chelating agent 14, the microcapsule 15 that has the core 16 containing the ionically-bonded polymer sol and the skeleton material is obtained by subjecting the core 8 to the step of solating the core 8. Such a microcapsule 15 has a higher capsule strength due to the skeleton material while maintaining internal diffusion in the core by the ionically-bonded polymer sol. For example, in a case where the core 8 is a core of an alginate gel that has been prepared by mixing alginate and cellulose insoluble in EDTA (the skeleton material), a cellulose support structure remains inside the core 16 of an alginate sol after the alginate is solubilized in EDTA (i.e., after solation of the alginate gel). A gel commonly has a pore size that is proportional to a concentration and/or a molecular weight of a polymer forming the gel. Thus, alginate that has a low concentration or a high molecular weight, or alginate that has a low concentration and a high molecular weight is used to prepare a porous core, mix the porous core with agarose, and then gel a resultant mixture in an emulsion. Solation of the alginate with use of EDTA allows preparation of a microcapsule that has therein an agarose porous structure.

The microcapsule 15 can have a particle size and a shell thickness that are selected in accordance with the size and/or an application of the embedding target object. The microcapsule 15 that has a particle size in a range of 10 µm to 500 µm is suitably used for gene amplification and cell culture.

(Target Object to be Embedded)

A target object to be embedded is not particularly limited and can be stably retained in a case where the target object is a substance that is larger than a mesh of the shell 17 of a thermoresponsive gel. For example, the target object can be a biological material such as high-molecular-weight DNA, a virus, or a microorganism. The target object can be a cell, and the cell can be a living cell or a dead cell. The cell can be contained in a state in which cells are individually dispersed, or can be contained in a state in which a plurality of cells are aggregated (e.g., in a state of some of a tissue or a cell mass). The cell is not particularly limited in origin, and examples of the cell include an animal; a plant; and fungi such as yeast. The cell can be not only a tissue-derived sample or a clinical sample but also a cultured cell. Alternatively, the cell can be, for example, any of an adult stem cell, an embryonic stem cell, and an induced Pluripotent Stem cell, or a cell differentiated from the adult stem cell, the embryonic stem cell, or the induced Pluripotent Stem cell.

The method for producing a microcapsule in accordance with an aspect of the present invention makes it possible to provide a hollow hydrogel microcapsule that can be stably retained while damage to and/or contamination of a target object is prevented or reduced.

<2. Kit>

A kit in accordance with an aspect of the present invention is a kit for use in a method for producing a hollow hydrogel microcapsule in accordance with an aspect of the present invention.

The kit includes, as essential components, raw material powder of the ionically-bonded polymer (e.g., alginate), alkaline earth metal carbonate (e.g., calcium carbonate) for gelling the ionically-bonded polymer gel, acid (e.g., acetic acid) for dissolving alkaline earth metal salt, a material of the oil phase for dispersing the ionically-bonded polymer, raw material powder of the thermoresponsive polymer (e.g., low melting point agarose), and a material of the oil used to form the shell of the thermoresponsive polymer, and a chelating agent for solating the ionically-bonded polymer gel. The material of the oil phase can contain a surfactant in advance.

The kit can further include a manual for producing any of the compositions described earlier. For example, a procedure described in the section <1. Method for producing microcapsule> (described earlier) is recorded in the manual. The manual is not particularly limited in form but can be, for example, a manual that is printed on a medium such as paper, or a manual that is electronically recorded on a recording medium.

The kit in accordance with an aspect can be configured such that the raw material powder of the shell of the thermoresponsive polymer (e.g., low melting point agarose, commonly available) and the raw material powder of the sol of the ionic polymer (e.g., alginate, commonly available) are separately purchasable by describing, in the manual, dosage and administration, etc. of the raw material powder of the sol of the ionic polymer and the raw material powder of the shell of the thermoresponsive polymer.

Use of the kit in accordance with an aspect makes it possible to provide a hollow hydrogel microcapsule containing a target object such as DNA, a microorganism, or a cell. Furthermore, a micromanipulator, a cell sorter, or the like can be used to isolate the hollow hydrogel microcapsule, containing such a target object, while protecting the hollow hydrogel microcapsule from environmental contamination.

After subjecting the target object to an enzyme reaction, culture, or a reaction with any reagent in the hollow hydrogel microcapsule, the hollow hydrogel microcapsule can be similarly isolated so that the content is subjected to an analysis.

<3. Amplification Method>

Next, the following description will more specifically discuss a reaction method in accordance with an aspect of the present invention. According to the reaction method in accordance with the present embodiment, an enzyme is used to amplify a biological material in a microcapsule that has been produced by the method described in <1. Method for producing microcapsule> (described earlier). In an aspect, the kit described in <2. Kit> can be used to produce the microcapsule. Note here that the biological material is preferably, for example, high-molecular-weight DNA.

Figure 3:
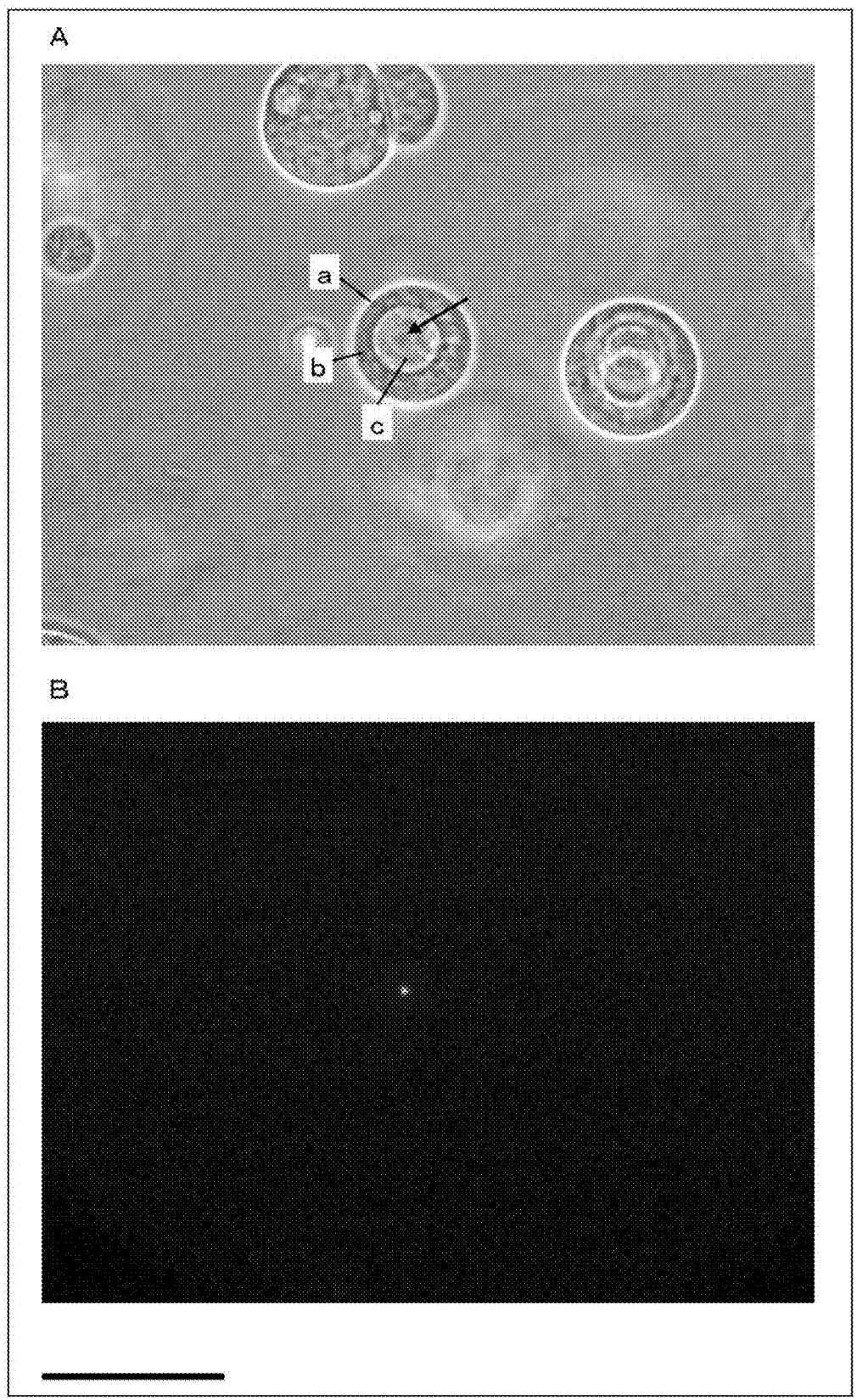
FIG. 3 is microscopic images of an AGM, which is an aspect of a hollow hydrogel microcapsule. A of FIG. 3 is a phase contrast observation image. a indicates an AGM, b indicates an agarose hydrogel shell, c indicates a hollow core made of an alginate sol, and an arrow indicates E. coli isolated in the AGM. B of FIG. 3 is a fluorescent observation image.

As illustrated in FIG. 3, a hollow hydrogel microcapsule has a shell made of a thermoresponsive polymer gel having a diameter of approximately 100 µm. The hollow hydrogel microcapsule causes the shell to prevent another high-molecular-weight DNA, a virus, a cell, a microorganism, or the like, from being mixed in a hollow sol in the microcapsule which hollow sol embeds the high-molecular-weight DNA. Meanwhile, materials that can be transmitted through the shell and are necessary for nucleic acid amplification, such as a buffer solution, magnesium salt, an enzyme (DNA polymerase), a reaction substrate (dNTP), and an RNA primer or a DNA primer are supplied so that the high-molecular-weight DNA can be uniformly amplified in a minute hollow sol space in the microcapsule. Thus, an amplification bias can be suitably prevented or reduced in the shell of the thermoresponsive polymer.

More specifically, an amplification method in accordance with an aspect can be whole genome amplification (WGA) in which Phi29 DNA polymerase is used to amplify the high-molecular-weight DNA as template DNA (template). For example, Phi29 DNA Polymerase Set (KANTO CHEMICAL CO., INC.), REPLI-g Ultrafast Mini Kit (QIAGEN N.V.), and the like can be used for whole genome amplification.

According to the amplification method in accordance with an aspect, in the first amplification, a fluorescence cell sorter, a micromanipulator, or the like is used to isolate a microcapsule in which it is observed by fluorescence staining that the microcapsule includes a single bacterial cell and that DNA is amplified. The amount of collected DNA in the microcapsule is as small as approximately 1 mg. Thus, it is possible to obtain several µg of amplified DNA necessary for an analysis of a next generation DNA sequencer by carrying out the second amplification in a microtube after further dissolving the shell. Examples of a DNA sequencer include next generation DNA sequencers such as MiSeq™ (Illumina, Inc.), HiSeq™ (Illumina, Inc.), and Ion PGM™ (Thermo Fisher Scientific).

<4. Delivery Agent>

In an aspect, the present invention is a method for producing a delivery agent, the method including the production method described in <1. Method for producing microcapsule>, and the delivery agent in which a microorganism or a cell is to be embedded is produced. In a case where a microorganism is to be embedded, a lactic acid bacterium or an intestinal cell from a healthy person is embedded in, for example, a hollow hydrogel microcapsule and administered to a patient so that such a microorganism is fixed in an intestinal environment and the intestinal environment is improved. As compared with direct oral administration, embedding into a microcapsule causes diffusion or outflow from inside the intestines to be less likely to occur. This makes it possible to expect an increase in retention rate.

In a case where a stem cell such as an adult stem cell is embedded in a hollow hydrogel microcapsule so as to be transplanted into an affected part, diffusion of shell permeable humoral factors allows promotion of activation and healing of peripheral tissues while causing a shell to prevent attack from an immune system cell. The microcapsule, which is hollow, also has an advantage such that mutual adhesion of cells allows the cells to survive at a higher rate due to scaffold formation. Furthermore, the microcapsule, which has a small capsule diameter and can be transplanted by injection or instillation, has convenience such as prevention of cell death by transmission of a nutrient and oxygen.

Particularly in a case where agarose is used for the shell, low biological toxicity of the agarose is also suitable for transplantation.

Moreover, in regenerative medicine, transplantation of a cell, generated by induced differentiation of a stem cell and embedded in a hollow hydrogel microcapsule having an agarose shell, not only has the convenience (described earlier) but also allows cells inside to be released to outside the microcapsule by mechanical breaking of the shell, having a thickness as small as several to several ten μm, caused by cell proliferation, so as to be formed into a final biological tissue.

<5. Library of Hydrogel Microcapsules>

A hydrogel microcapsule that is produced in an embodiment of the present invention can be a library composed of a plurality of hydrogel microcapsules in each of which the target object is embedded. The hydrogel microcapsules can differ in target object to be embedded. The number of hydrogel microcapsules of which the library is composed is not particularly limited, but is, for example, in a range of 10 to $10^{10}$, or in a range of 100 to $10^9$.

<6. Single Cell Analysis>

A hydrogel microcapsule produced in an embodiment of the present invention can also be used for a single cell analysis. For example, appropriate control of a concentration of a cell contained in a solution for preparing a core of a microcapsule makes it possible to cause a single cell to be embedded in each hydrogel microcapsule with a high probability (see also Examples). The single cell analysis is not particularly limited in type. An analysis method can also be selected as appropriate in accordance with an analysis target and is exemplified by an analysis of a gene possessed by a cell, an analysis of protein, and an analysis of other metabolite.

For example, in a case where a cell to be embedded in a hydrogel microcapsule is a microorganism, the present invention can be used for isolation of an effective microorganism and an analysis of the effective microorganism. As a more specific example, the present invention is used to, for example, monitor the intestinal environment. Assuming, for example, that an intestinal bacterial flora is a monitoring target, a library of hydrogel microcapsules in each of which a single microorganism is embedded is prepared. It is possible to, for example, monitor the intestinal environment by using the library to analyze, for example, (i) a type of enteric bacteria constituting the intestinal bacterial flora and (ii) a presence ratio (a percentage accounting for the intestinal bacterial flora) of enteric bacteria of a certain type.

The present invention can also be used in a medical field. For example, in the field of cancer diagnosis, a library of hydrogel microcapsules is prepared in which cells contained in a tissue sample (that can be a humoral sample such as blood or lymph) collected from a subject are individually embedded. The library is used to analyze, for example, the presence or absence of a cancer cell, a presence ratio of cancer cells, and a characteristic of a cancer cell. The cancer cell can be a circulating tumor cell (CTC). The present invention can be used not only to diagnose whether a cancer is present, but also to, for example, select a treatment in a case where a cancer is present.

In the medical field, the present invention can also be used to control a quality of therapeutic cells. For example, a library of hydrogel microcapsules in which therapeutic cells are individually embedded is prepared. The library is used to analyze, for example, characteristics of those cells and the presence ratio of non-defective/defective cells. Examples of the therapeutic cells include therapeutic stem cells (including multipotent stem cells) in the field of regenerative medicine and cells differentiated from those stem cells. Other examples of the therapeutic cells include therapeutic cells accompanying genetic modification, such as induced Pluripotent Stem (iPS) cells (also serving as therapeutic stem cells), CAR-T cells, and cells for gene therapy (e.g., cells into which genes missing in a patient have been introduced so as to be expressible).

In the field of gene diagnosis, for example, hydrogel microcapsules are prepared in which cells collected from a subject to undergo gene diagnosis are embedded. The hydrogel microcapsules are used to carry out a gene analysis of the cells (the gene analysis can be an analysis of a specific target gene or a whole genome analysis) so as to obtain analytical data for use in gene diagnosis. The gene diagnosis includes, for example, (i) diagnosis of susceptibility to, for example, gene-related diseases and (ii) diagnosis of drug-related sensitivity (e.g., whether a drug is highly likely to be effective, selection of a drug in the treatment of diseases such as cancer).

As compared with an analysis carried out by isolation of a single cell with use of, for example, a cell sorter, a single cell gene analysis carried out with use of hydrogel microcapsules obtained in the present invention is more advantageous in that an amplification bias is less likely to occur during gene amplification (see also Examples). Unlike the present invention, according to an existing technique (emulsion WGA) for carrying out genome amplification in droplets, it is impossible to carry out an analysis in units of specific cells. Furthermore, according to the existing technique, it is difficult to carry out the whole genome analysis due to a small amount of gene amplification.

Figure 5:
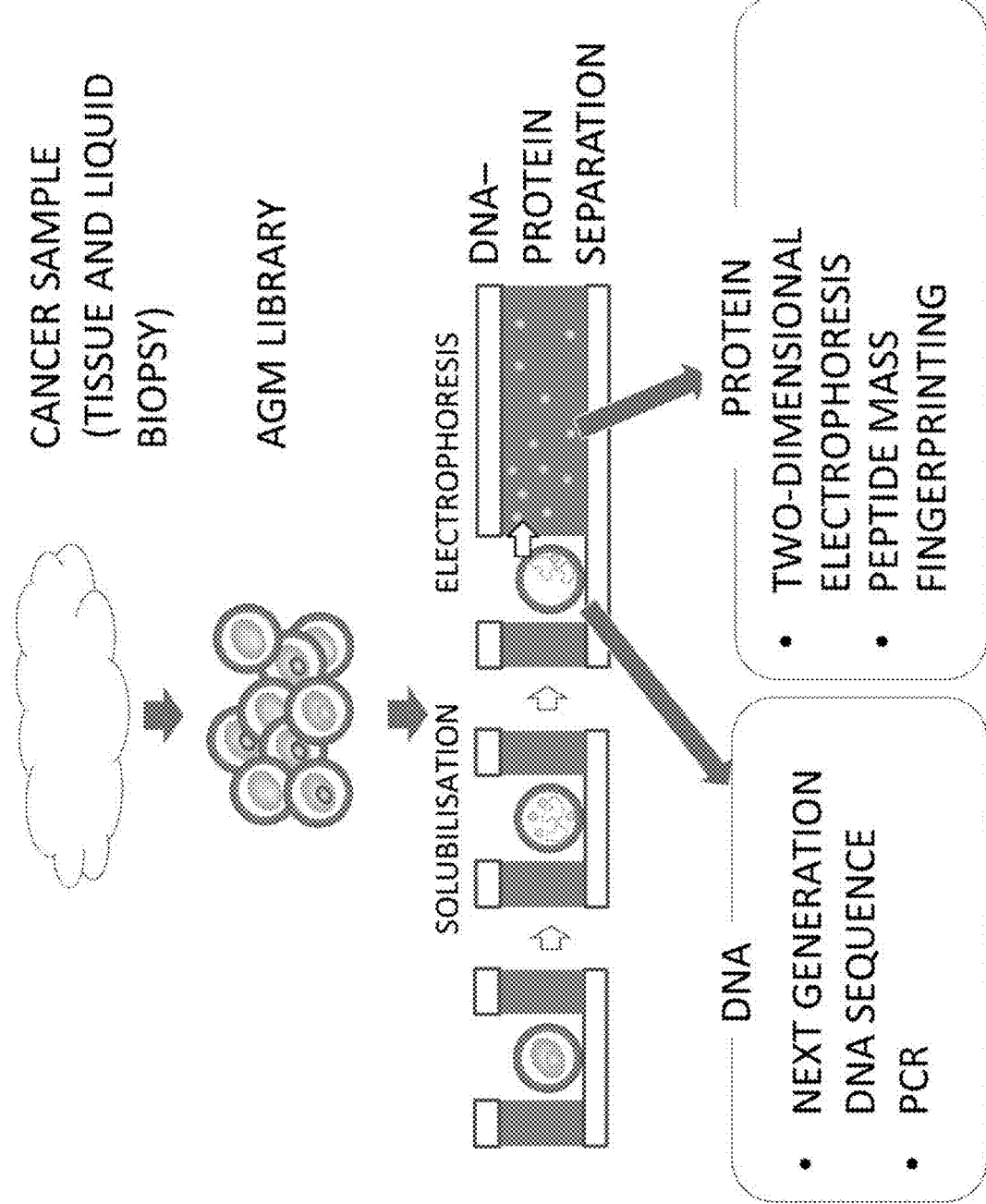
FIG. 5 is a view schematically illustrating an example of a single cell analysis.

FIG. 5 illustrates a specific example of the single cell analysis. In this example, a library of hydrogel microcapsules (AGMs) is prepared in which cells contained in a tissue sample collected from a subject (e.g., a person undergoing diagnosis of cancer) are individually embedded. Next, the AGMs constituting the library are stored one by one in microwells. Subsequently, the cells embedded in the AGMs are lysed by, for example, an osmotic pressure, a surfactant, or alkali while being stored in the AGMs (lysis). Then, the AGMs containing the lysed cells are used for various analyses. Since a method is publicly known in which only protein or only nucleic acid (DNA) is separated so as to be analyzed, the present invention makes it possible to simultaneously analyze only protein or only nucleic acid (DNA) contained in a single cell, or both the protein and the nucleic acid (DNA). Note that a publicly-known method such as electrophoresis can be employed as appropriate to separate a desired component(s) from a composition containing protein and nucleic acid. Nucleic acid (DNA), which is a macromolecule, cannot pass through a semipermeable shell of a hydrogel microcapsule, whereas protein, which has a lower molecular weight than nucleic acid (DNA), can pass through the shell of the hydrogel microcapsule. This allows effective separation of protein and nucleic acid (DNA) of a single cell. Protein and nucleic acid (DNA) can also be analyzed by a publicly-known method. Examples of a method of analyzing protein include a two-dimensional electrophoresis method, a peptide mass method, and a fingerprinting method.

<7. System for Producing Hydrogel Microcapsule>

Figure 6:
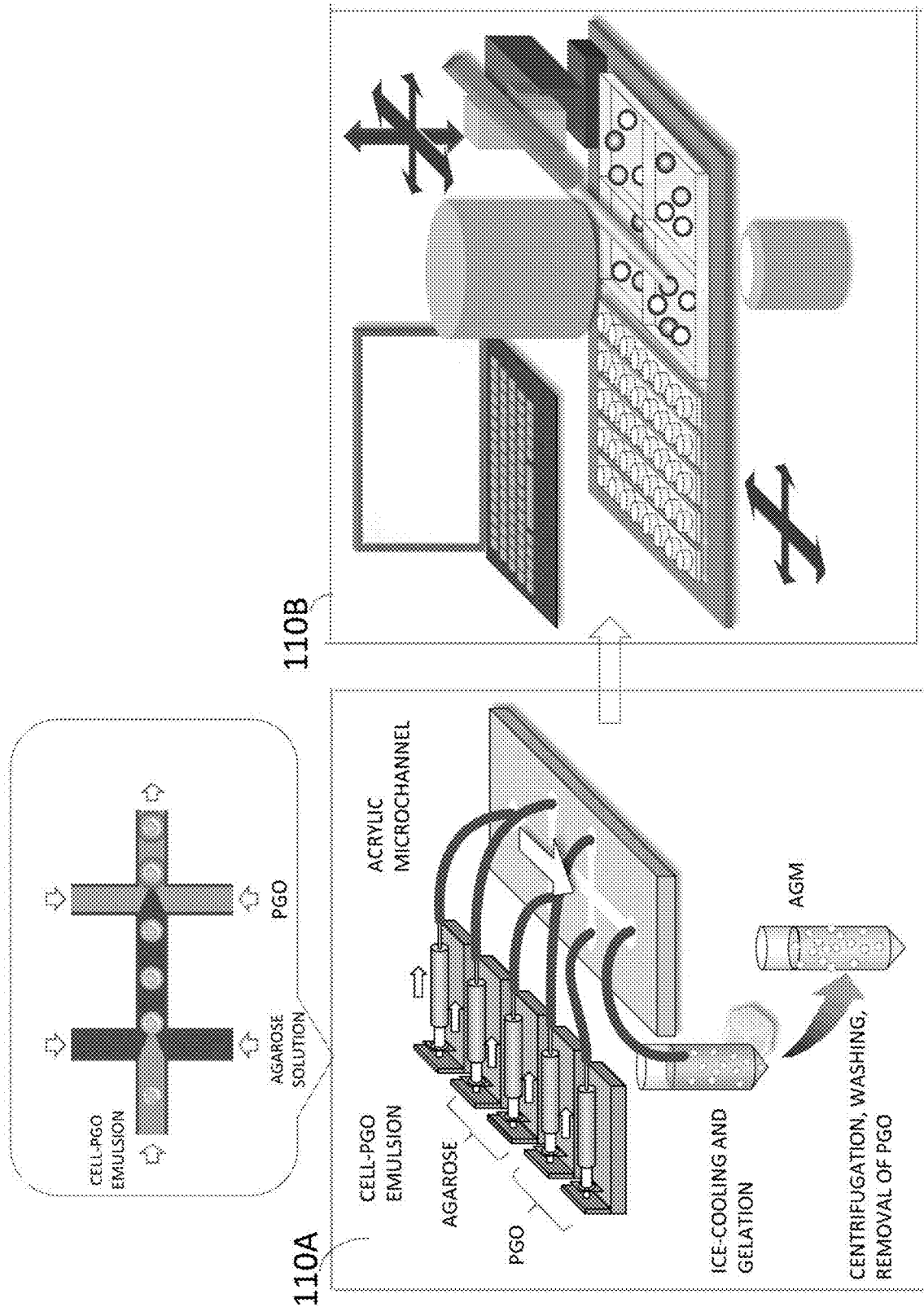
FIG. 6 is a view illustrating a system for producing a hollow hydrogel microcapsule in accordance with an aspect of the present invention.

The following description will discuss, with reference to FIG. 6, an example of a system for producing a hollow hydrogel microcapsule in accordance with an aspect of the present invention. This production system is configured to carry out the production method described in <1. Method for producing microcapsule> and to include a microcapsule production device 110A.

The microcapsule production device 110A includes a microchannel for mixing different liquids. The microchannel is constituted by, for example, a main channel and two sub-channels intersecting (orthogonal to) the main channel. The main channel and the two sub-channels are provided on a resin substrate such as an acrylic resin substrate. The two sub-channels are (i) a first sub-channel located upstream of the main channel and (ii) a second sub-channel located downstream of the main channel. A hydrogel microcapsule in which a cell is embedded is produced by pouring, from upstream of the main channel, a cell-oil emulsion (the emulsion obtained through the steps of (a) to (c) of FIG. 1 and containing the oil 5 and the beads 8 of the ionically-bonded polymer gel in which the cells are embedded). From the first sub-channel, a sol of a thermoresponsive polymer (an agarose solution) is poured so that a suspension is obtained in which droplets of the cell-oil emulsion are suspended in the sol (corresponding to (d) of FIG. 1). From the second sub-channel, oil (e.g., PGO) is poured so that a suspension of a thermoresponsive polymer sol and oil are emulsified and the minute droplets 11 of the thermoresponsive polymer sol which minute droplets 11 contain the beads 8 are prepared (corresponding to (e) of FIG. 1). Use of the microchannel makes it possible to easily prepare the minute droplets 11 that are more uniform.

For example, a cooling device is provided so as to follow the microchannel. The prepared minute droplets 11 of the thermoresponsive polymer sol are collected from the main channel downstream side of the microchannel, and those minute droplets 11 are ice-cooled in the cooling device so that the thermoresponsive polymer sol is gelled (corresponding to (f) of FIG. 1).

A collection device (e.g., a centrifugation device) for collecting hollow hydrogel microcapsules is provided so as to follow the cooling device. In the collection device, an operation such as centrifugation is carried out so that hollow hydrogel microcapsules 15 are collected from the oil and washed, and then the hollow hydrogel microcapsules 15 are suspended in the buffer solution 13 (corresponding to (g) of FIG. 1).

Note that a series of operations carried out by the microcapsule production device 110A is preferably automated through computer control.

The system for producing a hollow hydrogel microcapsule can further include a picker (selection device) 110B, provided so as to follow the microcapsule production device 110A, for picking the microcapsules 15. The picker 110B selects a microcapsule 15 that satisfies a desired requirement. The picker 110B selects, for example, 1) a non-defective microcapsule 15 produced by the microcapsule production device 110A, or 2) a desired one(s) of the microcapsules 15 used for an analysis (e.g., only the one(s) in which WGA is observed).

The picker 110B dispenses the selected microcapsule(s) 15 into, for example, a storage vessel such as microwells. Note that a series of operations carried out by the picker 110B is preferably automated through computer control. Automation of control makes it easy to carry out the operations under a germ-free environment.

<8. Additional Remarks>

According to various aspects of the present invention illustrated herein, all the steps can be carried out by a single subject, or some of the steps can be carried out by different subjects. For example, in <1. Method for producing microcapsule> (described earlier), the step of preparing (Target object to be embedded) (referred to as a "step A") can be carried out by a certain subject, and the step of producing a hollow hydrogel microcapsule in which the target object is embedded (referred to as a "step B") can be carried out by an entrusted manufacturer different from the certain subject. The entrusted manufacturer possesses <7. System for producing hydrogel microcapsule> (described earlier) and raw materials of the system.

The step of using and analyzing the hollow hydrogel microcapsule in which the target object is embedded (referred to as a "step C") can also be carried out by a subject different from those who carry out the steps A and B. The step C corresponds to, for example, <3. Amplification method> (described earlier) and <6. Single cell analysis> (described earlier), and can be carried out by, for example, an entrusted inspection agency. Reagents necessary for amplification and an analysis can be prepared by an entruster, or can be procured by the entrusted inspection agency.

Aspects of the present invention can also be expressed as follows:

The present invention includes, for example, the following aspects.

1) A method for producing a hydrogel capsule including (i) a core containing an ionically-bonded polymer and (ii) a shell containing a thermoresponsive polymer, the method including:

(a) cooling a suspension so as to gel the thermoresponsive polymer and form the shell, the suspension being obtained by suspending, in a first oil phase, a sol (aqueous phase) of the thermoresponsive polymer including a core at least a surface of which is formed from a gel of the ionically-bonded polymer, oil, contained in the first oil phase, having a hydrophobicity, as measured by an octanol-water partition coefficient (Log $P_{ow}$), of not less than 3 and having a specific gravity and a viscosity that satisfy the following formula:

$$\rho_p - \rho_f \leq \frac{18(100-x)L}{100 t D_p^2 g}\eta$$

wherein $\rho_p$ represents an average specific gravity [kg/m$^3$] of an ionically-bonded polymer gel and a thermoresponsive polymer sol; $\rho_f$ represents an oil specific gravity [kg/m$^3$]; x represents a yield [%] obtained in a step of producing the hydrogel capsule; L represents a depth [m] of the suspension that is contained in a vessel; t represents a gelling time [s] of the thermoresponsive polymer; $D_p$ represents a diameter [m] of the hydrogel capsule; g represents gravitational acceleration [m/s$^2$]; and η represents an oil viscosity [Pa·s].

2) The method recited in 1), wherein the hydrogel capsule is a hollow hydrogel capsule having an inner part in solution form. Alternatively, the hydrogel capsule can be a hydrogel capsule that has an inner part having a porous structure in solution form and containing a skeleton material.

3) The method recited in 2), wherein ions contained in the gel of the ionically-bonded polymer are removed after the step (a) so that the gel of the ionically-bonded polymer is solated.

4) A method recited in any one of 1) to 3), further including:

(b) before the step (a), dispersing a sol of the ionically-bonded polymer into a second oil phase that is different from the first oil phase, and supplying ions so as to gel at least a surface of the dispersed sol of the ionically-bonded polymer; and (c) dispersing, into the sol of the thermoresponsive polymer, the ionically-bonded polymer at least a surface of which has been gelled, the second oil phase containing a surfactant.

5) A method recited in any one of 1) to 4), further including:

(d) in order to collect the hydrogel capsule from the first oil phase, making the first oil phase lower in specific gravity than the aqueous phase and carrying out centrifugation.

6) The method recited in any one of 1) to 5), wherein the thermoresponsive polymer (i) is at least one kind of thermoresponsive polymer that forms a reversible gel and that is selected from the group consisting of agarose, carrageenan, agar, and gelatin, or (ii) is collagen.

7) The method recited in any one of 1) to 6), wherein the ionically-bonded polymer is at least one kind of ionically-bonded polymer that forms a reversible gel and that is selected from the group consisting of alginate, polysaccharides, polyacrylic acid, and carboxymethylcellulose.

8) The method recited in any one of 1) to 7), wherein the first oil phase is an oil phase that contains polyglycerol fatty acid ester.

9) The method recited in any one of 1) to 8), wherein a target object is embedded in the core of the ionically-bonded polymer.

10) The method recited in 9), wherein the target object is a biological material selected from the group consisting of a microorganism, a cell, a virus, and high-molecular-weight DNA.

11) The method recited in any one of 1) to 10), wherein the first oil phase contains a surfactant.

12) A kit for producing a hydrogel capsule recited in any one of 1) to 11), the kit including:

a material of the ionically-bonded polymer;

a material of the thermoresponsive polymer; and a material of the first oil phase.

13) A method including amplifying the biological material after a step of carrying out a method recited in 10), the biological material being high-molecular-weight DNA.

14) A method for producing a delivery agent, including a method recited in 10), the target object to be embedded being a cell or a microorganism.

15) A device for producing a hydrogel capsule recited in any one of 1) to 11).

16) A method for producing a hydrogel capsule recited in any one of 1) to 11), wherein a microchannel is used to produce a suspension obtained by suspending, in an oil phase, a sol (aqueous phase) of the thermoresponsive polymer including a core at least a surface of which is formed from a gel of the ionically-bonded polymer. In an embodiment, the microchannel includes channels which are provided so that the aqueous phase is produced by mixing (a) the core at least a surface of which is formed from a gel of the ionically-bonded polymer and (b) the sol of the thermoresponsive polymer and then the aqueous phase thus produced and the oil phase are mixed so that the suspension is obtained.

17) A production device or a production system for use in a method recited in 16), includes the microchannel. The production device or the production system can further include a cooling device for cooling the suspension and/or a collection device for collecting hydrogel capsules produced.

EXAMPLES

Example 1. Production of AGM with *E. coli* Embedded Therein and Serving as Example of Hollow Hydrogel Microcapsule In Examples below, a concentration is represented by a final concentration, unless otherwise specified.

First, a core of an alginate gel containing *E. coli* was prepared by an emulsification internal gelation method. Prepared was a 50 mM acetate buffer solution (pH 7.0) (alginate solution) containing an *E. coli* DH5 α strain ($3.05 \times 10^3$/mL, TAKARA BIO INC.), $CaCO_3$ powder (Shiraishi Kogyo Kaisha, Ltd.) at a concentration of 1% (w/v), and sodium alginate (Wako Pure Chemical Industries, Ltd.) at a concentration of 2% (w/v).

The alginate solution (1 mL) was suspended with isostearyl alcohol (ISA, KOKYU ALCOHOL KOGYO CO., LTD.) (9 mL), to which lecithin was added at a concentration of 3% (v/v), so as to be emulsified. ISA (1 mL) to which acetic acid was added, to the emulsified suspension, at a concentration of 2% (v/v) was gradually added while being stirred, so that alginate droplets were gelled. After diethyl ether (5 mL) was added to the suspension and the resultant suspension was suspended, a supernatant was removed by centrifugation carried out for 3 minutes at 2,000×g. After the suspension was suspended in a 50 mM TrisHCl buffer solution (pH 7.5) (5 mL) to which Tween (Registered Trademark) 20 was added at a concentration of 0.2% (w/v), 1-butanol (5 mL) was added to the suspension, and the resultant suspension was suspended so that a supernatant containing oil was removed by centrifugation (butanol washing). After being subjected to butanol washing again, the suspension was suspended in the TrisHCl buffer solution (5 mL) and filtrated through a 100 μm mesh cell strainer (Falcon) so that an aggregated alginate gel was removed. The filtrate was further washed with the TrisHCl buffer solution so that a core of the alginate gel was obtained.

Next, a shell of an agarose gel was formed on a surface of the core of the alginate gel. The core of the alginate gel (0.3 mL) was suspended in heat-dissolved 2% (w/v) low melting point agarose (SeaPlaque™ agarose, LONZA KK.) (1 mL) and kept warm at 35° C. The resultant suspension was suspended until the suspension was uniformly mixed with PGO (The Nisshin OilliO Group, Ltd.) (10 mL) to which Span (Registered Trademark) 80 was added at a concentration of 0.25% (w/v), and the suspension was emulsified. The resultant emulsified suspension and the PGO to which Span (Registered Trademark) 80 was added were mixed in equal proportions, and the resultant mixture was gelled on ice for 30 minutes. Thus, a microcapsule having the core of the alginate gel in a central part thereof and the shell of the agarose gel in a shell thereof was formed in the PGO. It is difficult to centrifuge the PGO and the microcapsule, which are substantially equal in specific gravity. Thus, after a specific gravity of an oil phase was lowered by mixing diethyl ether (10 mL) with the PGO containing the microcapsule, centrifugation was carried out so that the oil phase and the microcapsule were separated. After the oil phase was removed, the microcapsule was suspended in TE (10 mL) to which 0.2% (v/v) Tween (Registered Trademark) was added, and was subjected to butanol washing carried out twice, so that the PGO was removed.

The following description will show that the operations carried out in the Example described above satisfy a condition represented by Formula (3).

$$\rho_p - \rho_f \leq \frac{18(100-x)L}{100 t D_p^2 g} \eta \quad (3)$$

Values of parameters based on a condition of Example 1 and defined in Formula (3) are as follows.
[Average Specific Gravity of Ionically-Bonded Polymer Gel and Thermoresponsive Polymer Sol: $\rho_p$]
An average specific gravity of a 2% (w/v) alginate gel and a 2% (w/v) low melting point agarose suspension is as follows.
$\rho_p$: 1,020 kg/m³ (20° C.)
A suspension of the alginate gel and the 2% (w/v) low melting point agarose suspension is hereinafter also referred to as an "agarose suspension".
[Oil Specific Gravity: $\rho_f$]
A specific gravity of PGO used as oil is as follows.
$\rho_f$: 997 kg/m³ (20° C.)
[Oil Viscosity: $\eta$]
A viscosity of the PGO (described earlier) is as follows.
$\eta$: 0.196 Pa·s (20° C.)
[Depth of Suspension: L]
A 50 mL conical tube used to suspend a suspension of the agarose suspension and the PGO to which Span (Registered Trademark) 80 was added (hereinafter also referred to as an "oil suspension") was erected upright, and a depth from a liquid surface to a bottom of the oil suspension contained was calculated as a depth of the suspension.
L: 0.040 m
[Gelling Time of Thermoresponsive Polymer: t]
Gelling time calculated from change in turbidity caused by gelation (literature value) t: 3,600 seconds (60 minutes)
[Yield of Microcapsules: x]
A yield of microcapsules was calculated from the obtained microcapsule amount relative to an added amount (weight ratio).
x: 88%
Note that a mixed solution obtained by mixing 10 mL of diethyl ether with 20 mL of PGO has a specific gravity of 902 kg/m³ (20° C.). Specifically, the specific gravity $\rho_f$ of oil was reduced from 997 kg/m³ to 902 kg/m³, and the viscosity n of the oil was lowered from 0.197 Pa·s to 0.131 Pa·s, so that the microcapsules were collected from the oil suspension.
[Diameter of Capsule: $D_P$]
A diameter of a capsule was calculated by microscopic observation.
$D_P$: 39.2±9.8×10⁻⁶ m
The following Formula (5) is derived from Formula (3). In a case where numerical values are substituted in Formula (5), the oil specific gravity $\rho_f$ is calculated as below.

$$\rho_p - \rho_f \leq \frac{18(100-x)L}{100 t D_p^2 g} \eta \quad (5)$$

$$\rho_f \geq 704 \text{ kg/m}^3$$

The above formula can be satisfied because PGO has a specific gravity of 997 kg/m³.

[Octanol-Water Partition Coefficient]
An octanol-water partition coefficient (Log $P_{ow}$) of PGO calculated with use of ChemDraw (Cambridge Software) was 26.3.

As described above, a method for producing a microcapsule of Example 1 satisfies the requirement represented by Formula (3), and it was successfully confirmed that satisfaction of the requirement that the octanol-water partition coefficient is not less than 3 makes it possible to (i) prevent precipitation and coagulation of a microcapsule during gelation of a thermoresponsive polymer in the microcapsule and (ii) easily prepare a microcapsule.

Finally, an alginate gel core was solated so that an AGM, which is a hollow hydrogel microcapsule, was prepared. A ¹⁄₁₀ (v/v) amount of 0.5 M EDTA was added to the microcapsule so that an alginate core was solated. The microcapsule to which the EDTA was added was filtered through a filter having a pore size of 300 μm, so that a large gel was removed. Then, filtration was carried out through a filter having a pore size of 10 μm, so that a small microcapsule was removed. The filtrate was further washed with TE so that an AGM was obtained.

The AGM was stained with SYBR Green I (Thermo Fisher Scientific), which is a DNA-binding fluorescence reagent, and a microscope was used to observe the shape of the AGM by phase contrast observation and to observe E. coli in the AGM by fluorescent observation. FIG. 3 shows results. In FIG. 3, A is a phase contrast image, B is a fluorescence image, and a bar represents 100 μm. In A illustrated in FIG. 3, (a) indicates a hollow hydrogel microcapsule, (b) indicates a shell of an agarose gel, (c) indicates a core of an alginate sol, and an arrow indicates embedded E. coli. The AGM thus containing a single E. coli cell was successfully prepared. Furthermore, the AGM had a diameter of 64 μm, had a core diameter of 38 μm, a volume of 29 μL, and an average shell thickness of 13 μm.

Example 2: WGA in AGM

WGA was carried out in a hollow hydrogel microcapsule containing a single bacterial cell, and the hollow hydrogel microcapsule was compared with an AGM in which no bacterial cell is embedded.

First, an AGM (250 μL) to which E. coli of Example 1 was added and an equal amount of a D1 buffer solution (QIAGEN N.V., REPLI-g Ultrafast Mini Kit) were mixed together, and lysis of the E. coli and denaturation of genomic DNA were carried out with use of alkali on ice for minutes. Then, an equal amount of an Ni buffer solution (QIAGEN N.V., REPLI-g Ultrafast Mini Kit) was added, and the resultant mixture was neutralized on ice for 30 minutes. The mixture was centrifuged at 2,000×g for 3 minutes and then a supernatant was removed. Thereafter, in order that the residue would be washed, after being suspended with a TE buffer solution (1 mL), the mixture was similarly centrifuged, and then a supernatant was removed. Washing was carried out by repeating twice the above operation for washing, so that an alkaline-denaturated AGM was obtained.

Next, a Phi29 DNA polymerase kit (KANTO CHEMICAL CO., INC.) was used to react the alkaline-denaturated AGM (24.4 μL) at a total volume of 50 μL for 16 hours at 30° C. so that WGA was carried out. A ¹⁄₁₀ (v/v) amount of 0.5 M EDTA was added so that a reaction was stopped, and then washing with TE (250 μL) was carried out three times. Then, TE (25 μL) was added so that a WGA-treated AGM was obtained.

Figure 4:
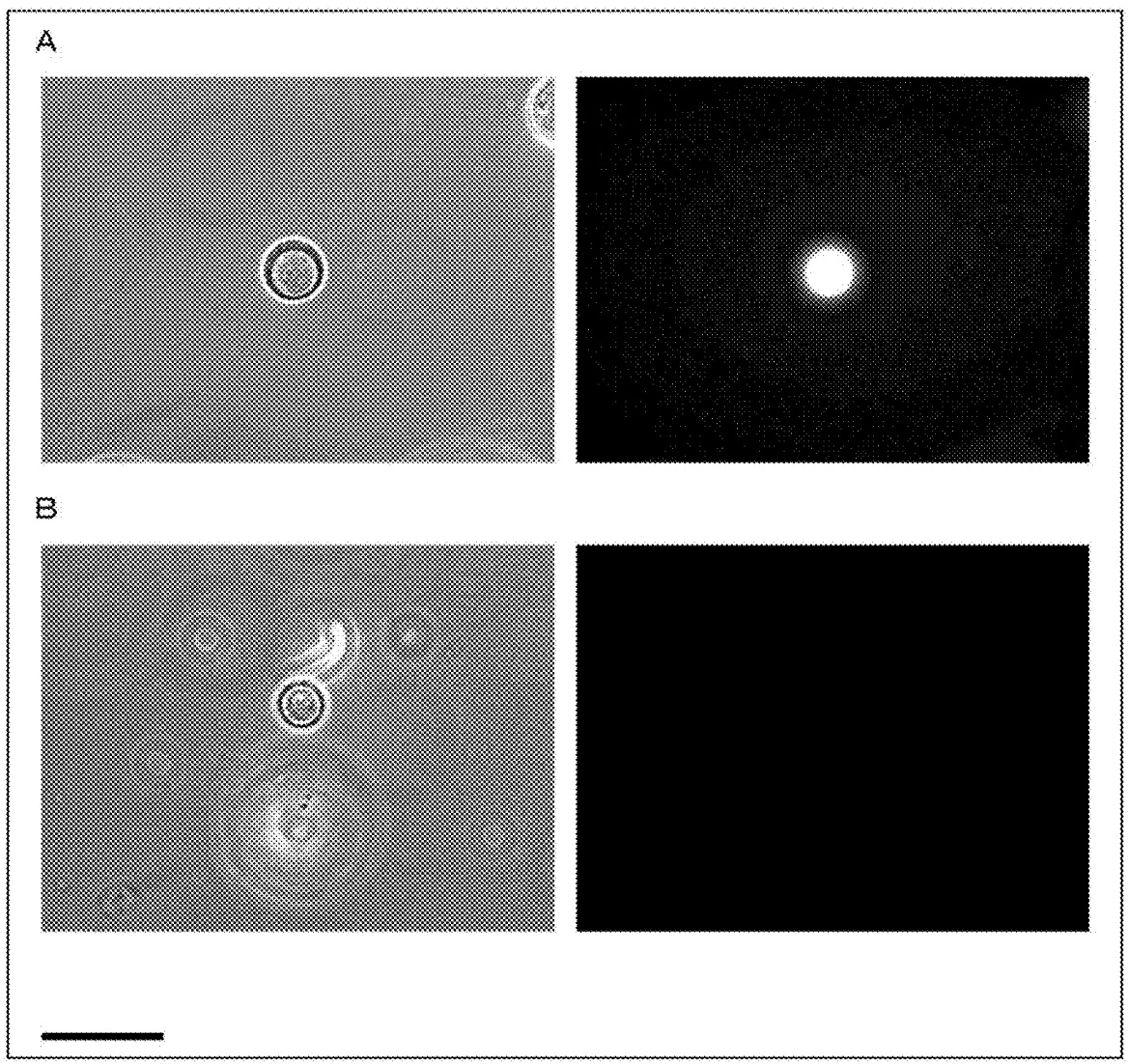
FIG. 4 is microscopic images in which whole genome amplification by an enzyme in an AGM, which is an application of the present invention, is carried out and then DNA specifically amplified in an inner part of a capsule is detected. A of FIG. 4 is phase contrast and fluorescence microscopic images obtained in a case where whole genome amplification derived from a specific single bacterial cell is carried out in an AGM. B of FIG. 4 is phase contrast and fluorescent observation images obtained after whole genome amplification is carried out, as a comparative experiment, in an AGM containing no bacterial cell.

The shape of the AGM having been subjected to WGA and amplified DNA accumulated in the AGM and stained with SYBR Green I as in the case of Example 1 were subjected to phase contrast observation and fluorescent observation. FIG. 4 shows results. In FIG. 4, A illustrates the AGM having been subjected to WGA and containing *E. coli*, and B illustrates the AGM also having been subjected to WGA and containing no *E. coli*. The drawings on the left side are phase contrast images, the drawings on the right side are fluorescence images, and a bar represents 100 μm. DNA amplification of a core as a whole was observed only in the AGM containing *E. coli*.

Example 3: Preparation of Library of AGMs

Figure 7:
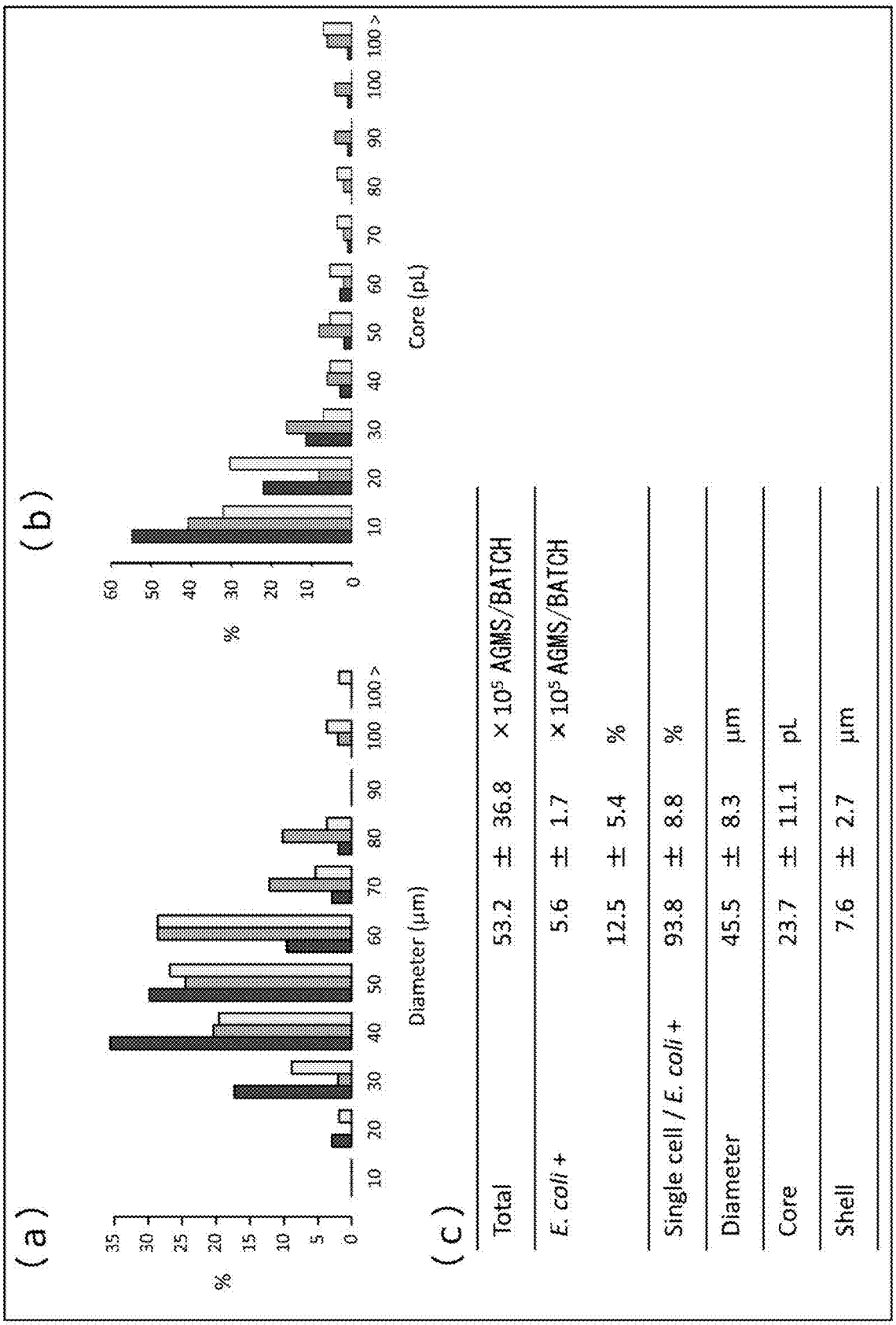
FIG. 7 is a view showing a result of preparation of a library of AGMs, the result being obtained in an example of the present invention.

AGMs in which *E. coli* cells were embedded were produced in accordance with the method described in Example 1, except that, in order that an AGM in which only one *E. coli* cell was embedded would be obtained with high efficiency, an alginate solution was prepared so that an *E. coli* DH5 α strain had a concentration of 30,000/mL. FIG. 7 shows results. (a) of FIG. 7 shows a distribution of a diameter (μm) of the AGMs produced, and (b) of FIG. 7 shows a distribution of a core volume (μL) of the AGMs produced. (c) of FIG. 7 shows a total number of AGMs obtained per batch (Total), the number of AGMs in which *E. coli* cells were embedded (*E. coli+*), an average diameter of the AGMs (Diameter), a core volume of the AGMs (Core), and a thickness of AGM shells (Shell). Single cell/*E. coli+* is a ratio (%) of AGMs each containing only one *E. coli* cell to the AGMs in which *E. coli* cells were embedded.

Example 4: WGA with Use of Library of AGMs

Figure 8:
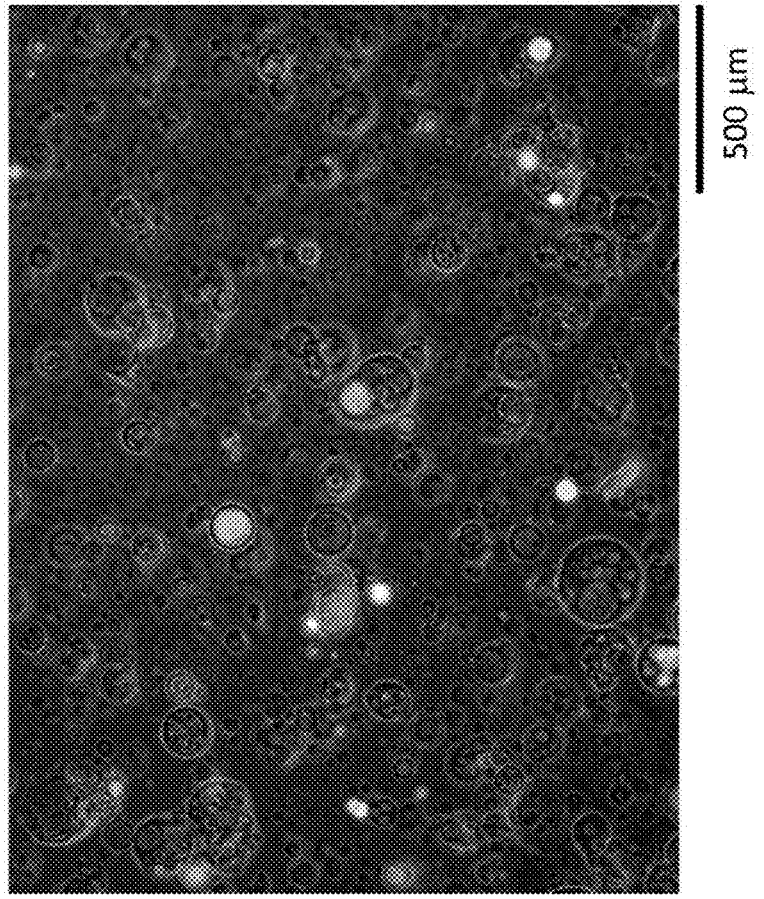
FIG. 8 is a view showing a result of WGA with use of a library of AGMs, the result being obtained in another example of the present invention.

The library of AGMs obtained by the method described in Example 3 was used to carry out WGA in the AGMs in accordance with the method of Example 2. FIG. 8 shows results. The table on the right side of FIG. 8 shows the number of AGMs, per batch, in which gene amplification was observed (WGA+) and a ratio (%) of those AGMs to the library of the AGMs, and a ratio (%) of AGMs in which gene amplification was observed to the AGMs in which *E. coli* cells were embedded (WGA+/*E. coli+*).

Example 5: Evaluation of DNA Amplification Bias

=Protocol=
(1) In accordance with the method described in Example 3, *E. coli* cells were diluted so that a single AGM contains a single bacterial cell, and a library of AGMs was prepared.
(2) REPLI-g Ultrafast Mini Kit (QIAGEN N.V.) was used to subject the library of AGMs (50 μl) to WGA. Specifically, the above library and a D1 buffer solution were mixed in substantially equal proportions so that lysis of the *E. coli* cells and alkaline denaturation of genomic DNA were carried out. Thereafter, an Ni buffer solution was added so that neutralization was carried out, and then 82.5 μl of a reaction solution (REPLI-g UltraFast Reaction buffer) and 11 μl of an enzyme (REPLI-g UltraFast DNA Polymerase) were added so that WGA was carried out at 30° C. for 30 minutes.
(3) Thereafter, a ⅒ volume of 0.5 M EDTA was added so that a reaction was stopped, and washing with TE was carried out three times.
(4) The library of AGMs was stained with SYBR Green I so that it was confirmed by fluorescent observation whether genomic DNA amplification was present. A micromanipulator was used to collect an AGM in which genomic DNA was amplified.
(5) The AGM in which genomic DNA was amplified was mixed with sterile water (29 μl) and then heated at 60° C. for 5 minutes so that a shell of an agarose gel was dissolved. Then, a sequence library to be analyzed in a step of (6) was prepared with use of QIAseq FX (QIAGEN N.V.) and in accordance with a protocol of the kit. Note, however, that a primer concentration was set to ⅒ the amount described in the protocol of the kit.
(6) MiSeq (Illumina, Inc.) was used to carry out a DNA analysis, and obtained data were compared in terms of a coverage ratio (Completeness, %) with respect to a chromosome as a whole.
As a comparative experiment, after a fluorescence cell sorter MoFLO (Beckman Coulter, Inc.) was used to isolate *E. coli*, the REPLI-g Ultrafast Mini Kit (QIAGEN N.V.) was used to carry out genome amplification of the *E. coli* in a microtube in accordance with a protocol of the kit (see also the steps of (2) and (3) (described earlier)). Then, a sequence library to be analyzed was prepared with use of QIAseq FX (QIAGEN N.V.) and in accordance with the protocol of the kit. Note, however, that a primer concentration was set to ⅒ the amount described in the protocol of the kit. MiSeq (Illumina, Inc.) was used to carry out a DNA analysis, and obtained data were compared in terms of a coverage ratio (Completeness, %) with respect to a chromosome as a whole.

=Result=
As a result of trial carried out 13 times (n=13), a coverage ratio (Completeness) of 36.5±17.9% was obtained in the comparative experiment, whereas a coverage ratio (Completeness) of 94.9±3.2% was obtained in the present Examples. This shows that the present Examples remarkably allow a region on an *E. coli* genome to be uniformly amplified.

INDUSTRIAL APPLICABILITY

The present invention can, for example, be used as a microcapsule for use in whole genome amplification and a delivery agent.

REFERENCE SIGNS LIST

1 Closed vessel
2 Ionically-bonded polymer sol
3 Embedding target object
4 Ion source
5 Oil for emulsification of ionically-bonded polymer sol
6 Minute droplet of ionically-bonded polymer sol
7 Organic acid
8 Ionically-bonded polymer gel beads
9 Thermoresponsive polymer sol
10 Oil for emulsification of thermoresponsive polymer sol
11 Minute droplet of thermoresponsive polymer sol containing ionically-bonded polymer gel beads
12 Thermoresponsive polymer gel beads containing ionically-bonded polymer gel beads
13 Buffer solution
14 Chelating agent
15 Hollow hydrogel microcapsule
16 Hollow core made of ionically-bonded polymer sol
17 Hydrogel shell made of thermoresponsive polymer gel

The invention claimed is:

1. A method for producing a hydrogel capsule including (i) a core containing an ionically-bonded polymer and (ii) a shell containing a thermoresponsive polymer, said method comprising:
(a) cooling a suspension so as to gel the thermoresponsive polymer and form the shell, the suspension being obtained by suspending, in a first oil phase, a sol (aqueous phase) of the thermoresponsive polymer including a core at least a surface of which is formed from a gel of the ionically-bonded polymer, oil, contained in the first oil phase, having a hydrophobicity, as measured by an octanol-water partition coefficient ($LogP_{ow}$), of not less than 3 and having a specific gravity and a viscosity that satisfy the following formula:

$$\rho_p - \rho_f \leq \frac{18(100-x)L}{100tD_p^2 g}\eta$$

wherein $\rho_p$ represents an average specific gravity [kg/m³] of an ionically-bonded polymer gel and a thermoresponsive polymer sol; $\pi r$ represents an oil specific gravity [kg/m³]; x represents a yield [%] obtained in a step of producing the hydrogel capsule; L represents a depth [m] of the suspension that is contained in a vessel; t represents a gelling time [s] of the thermoresponsive polymer; $D_p$ represents a diameter [m] of the hydrogel capsule; g represents gravitational acceleration [m/s²]; and n represents an oil viscosity [Pa·s].

2. The method as set forth in claim 1, wherein the hydrogel capsule is a hollow hydrogel capsule having an inner part in solution form, or has an inner part in solution form and containing a skeleton material.

3. The method as set forth in claim 2, wherein ions contained in the gel of the ionically-bonded polymer are removed after the step (a) so that the gel of the ionically-bonded polymer is solated.

4. A method as set forth in claim 1, further comprising:
(b) before the step (a), dispersing a sol of the ionically-bonded polymer into a second oil phase that is different from the first oil phase, and supplying ions so as to gel at least a surface of the dispersed sol of the ionically-bonded polymer; and (c) dispersing, into the sol of the thermoresponsive polymer, the ionically-bonded polymer at least a surface of which has been gelled, the second oil phase containing a surfactant.

5. A method as set forth in claim 1, further comprising:
(d) in order to collect, from the first oil phase, the shell that is formed by gelling the thermoresponsive polymer, making the first oil phase lower in specific gravity than the aqueous phase and carrying out centrifugation.

6. The method as set forth in claim 1, wherein the thermoresponsive polymer (i) is at least one kind of thermoresponsive polymer that forms a reversible gel and that is selected from the group consisting of agarose, carrageenan, agar, and gelatin, or (ii) is collagen.

7. The method as set forth in claim 1, wherein the ionically-bonded polymer is at least one kind of ionically-bonded polymer that forms a reversible gel and that is selected from the group consisting of alginate, polysaccharides, polyacrylic acid, and carboxymethylcellulose.

8. The method as set forth in claim 1, wherein the first oil phase is an oil phase that contains polyglycerol fatty acid ester.

9. The method as set forth in claim 1, wherein a target object is embedded in the core of the ionically-bonded polymer.

10. The method as set forth in claim 9, wherein the target object is a biological material selected from the group consisting of a microorganism, a cell, a virus, and high-molecular-weight DNA.

11. The method as set forth in claim 1, wherein the first oil phase contains a surfactant.

12. A kit for producing a hydrogel capsule recited in claim 1, said kit comprising:
a material of the ionically-bonded polymer;
a material of the thermoresponsive polymer; and
a material of the first oil phase.

13. A method comprising amplifying the biological material after a step of carrying out a method recited in claim 10,
the biological material being high-molecular-weight DNA.

14. A method for producing a delivery agent, comprising a method recited in claim 10,
the target object to be embedded being a cell or a microorganism.

15. A device for producing a hydrogel capsule recited in claim 1.

* * * * *